United States Patent
Chaudhry

(10) Patent No.: US 11,253,174 B2
(45) Date of Patent: Feb. 22, 2022

(54) APPARATUS FOR MEASURING THE CONCENTRATION OF TARGET SUBSTANCES IN BLOOD

(71) Applicant: Afon Technology Ltd., Monmouthshire (GB)

(72) Inventor: Sabih Chaudhry, Chepstow Monmouthshire (GB)

(73) Assignee: AFON TECHNOLOGY LTD, Caldicott (GB)

(*) Notice: Subject to any disclaimer, the term of this patent is extended or adjusted under 35 U.S.C. 154(b) by 361 days.

(21) Appl. No.: 16/103,977

(22) Filed: Aug. 16, 2018

(65) Prior Publication Data
US 2019/0053741 A1    Feb. 21, 2019

Related U.S. Application Data

(63) Continuation of application No. PCT/GB2017/050389, filed on Feb. 15, 2017.

(30) Foreign Application Priority Data

Feb. 17, 2016    (GB) .................................... 1602773

(51) Int. Cl.
    *A61B 5/145*    (2006.01)
    *A61B 5/0507*    (2021.01)
    (Continued)

(52) U.S. Cl.
    CPC ........ *A61B 5/14532* (2013.01); *A61B 5/0507* (2013.01); *A61B 5/1495* (2013.01);
    (Continued)

(58) Field of Classification Search
    CPC . A61B 5/14532; A61B 5/6824; A61B 5/7246; A61B 5/1495; A61B 5/6843;
    (Continued)

(56) References Cited

U.S. PATENT DOCUMENTS

| 5,508,203 A | 4/1996 | Fuller et al. |
| 5,661,404 A | 8/1997 | Yanagawa et al. |

(Continued)

FOREIGN PATENT DOCUMENTS

| EP | 2168518 A2 | 3/2010 |
| GB | 1193577 | 6/1970 |
| WO | 2014/207733 A1 | 12/2014 |

*Primary Examiner* — Allen Porter
*Assistant Examiner* — Abid A Mustansir
(74) *Attorney, Agent, or Firm* — Elmore Patent Law Group, P.C.; Joseph C. Zucchero; Carolyn S. Elmore

(57) ABSTRACT

A non-invasive testing apparatus for determining a concentration of a target substance, such as blood sugar, blood alcohol, cholesterol, etc., in a patient's blood is disclosed. The apparatus and method involve applying an output RF signal (102) to the skin of a patient via an antenna (20), and measuring the amplitude and phase of a response signal, which is a function of the output RF signal (102) modified by an interaction with the patient's blood. The invention takes measurements at different output RF frequencies (310), and plots the response (300) as a function of frequency (310). The invention is essentially characterised by deriving various derived parameters (552, 554, 556, 550, 408, 410) from the shape of the resulting plots, namely any or more of: a resonance frequency shift; a Q factor of the resonance; a group delay; a phase shift; an amplitude variation; a shape factor of the plot; and a gradient of the plot at different frequencies. The invention utilises models of the derived parameters as a function of concentration of the target substance in blood to arrive at a determination of the latter. Also disclosed is a novel circuit (1000) for obtaining the amplitude and phase measurements, a calibration device (5008), and various improvements relating to wearable non-invasive testing apparatus (3000, 4000).

20 Claims, 13 Drawing Sheets

(51) Int. Cl.
    *A61B 5/00*          (2006.01)
    *A61B 5/1495*      (2006.01)
    *A61B 5/05*         (2021.01)

(52) U.S. Cl.
    CPC .......... *A61B 5/14546* (2013.01); *A61B 5/681* (2013.01); *A61B 5/6824* (2013.01); *A61B 5/6831* (2013.01); *A61B 5/6843* (2013.01); *A61B 5/7246* (2013.01); *A61B 5/05* (2013.01); *A61B 5/72* (2013.01)

(58) Field of Classification Search
    CPC . A61B 5/6831; A61B 5/14546; A61B 5/0507; A61B 5/681; A61B 5/05; A61B 5/72; A61B 5/00
    See application file for complete search history.

(56) References Cited

U.S. PATENT DOCUMENTS

| | | |
|---|---|---|
| 2004/0147819 A1 | 7/2004 | Caduff et al. |
| 2007/0029989 A1 | 2/2007 | Haruta et al. |
| 2008/0319285 A1 | 12/2008 | Hancock |
| 2009/0275814 A1 | 11/2009 | Watanabe et al. |
| 2013/0085356 A1 | 4/2013 | Schlottau et al. |
| 2013/0225960 A1 | 8/2013 | Porch et al. |
| 2013/0289375 A1 | 10/2013 | Fischer |
| 2015/0112170 A1 | 4/2015 | Amerson, III et al. |
| 2016/0317060 A1* | 11/2016 | Connor .................. A61B 5/681 |

* cited by examiner

APPARATUS FOR MEASURING THE CONCENTRATION OF TARGET SUBSTANCES IN BLOOD

This application is a continuation of International Application No. PCT/GB2017/050389, which designated the United States and was filed on Feb. 15, 2017, published in English, which claims priority to GB Application No. 1602773.2, filed Feb. 17, 2016. The entire teachings of the above applications are incorporated herein by reference.

This invention relates to a method and apparatus for measuring the concentration of target substances in blood. In particular, the invention relates to a non-invasive method and apparatus for measuring blood sugar levels, or indeed the concentration of other desired target substances, such as blood alcohol, cholesterol, and so forth.

Diabetes mellitus (diabetes) is a disease in which the body does not produce or properly use insulin. Put simply, insulin is a hormone that the body uses to convert sugar and starches into energy. In other words, insulin is the hormone that unblocks cells of the body, allowing glucose to enter these cells to provide food to keep them alive.

People suffering from diabetes are known as diabetics, and diabetics suffer because as glucose (blood sugar) cannot enter their body's cells normally, glucose concentrations in the body (and in particular in the blood) build-up. Without appropriate and timely intervention/treatment, the cells within the body can end up being starved.

As such, many medical practitioners consider the measurement of blood-glucose as being perhaps one of the most important measurements in modern medicine due to the immense public health implications of diabetes. Diabetes is often cited as being one of the leading causes of disability and death throughout the world.

In order to prevent the onset and the progression of complications associated with diabetes, sufferers of both Type I and Type II diabetes are advised to closely monitor the concentration of glucose in their bloodstream. If the concentration is outside the normal healthy range, the patient needs to adjust his or her insulin dosage or sugar intake to counteract the risk of diabetic complications.

It is a recommendation of the medical profession that insulin-dependent patients practice self-monitoring of blood-glucose levels and then, based on the measured blood-glucose level, patients are able to make insulin dosage adjustments prior to injection. These adjustments are extremely important since blood-glucose levels vary over the period of a day due to a variety of reasons, for example, stress, exercise, types of food eaten, absorption rate for the food, long periods without food and hormonal changes.

Traditional methods of monitoring the blood-glucose level involve invasive or minimally invasive techniques.

Historically, and in certain situations, glucose monitoring can be achieved by urine analysis. This method tends to be inconvenient (as a patient needs to wait to urinate before a test can be performed, and the urine capture procedure can be messy and unhygienic) and may not reflect the current status of the blood-glucose level due to the fact that glucose appears in the urine only after a significant period of elevated levels of blood-glucose. This method was, in fact, used by physicians of the past where the diagnosis was made by tasting the patient's urine. U.S. Pat. No. 6,021,339 describes in detail a modern-day apparatus used for urine testing.

The most common method of measuring blood-glucose level nowadays requires blood to be withdrawn from the patient. The conventional procedure involves pricking the finger, or other body part, to withdraw blood, and then to deposit one or more drops onto a reagent carrier strip having a glucose testing substance thereon. The testing substances change colour or shading in response to the detected amount of blood-glucose. A colour chart is then used to determine the associated numerical value of blood-glucose. One of the technical short falls of this technique is that measurement sensitivity is somewhat limited due to the finite range of colours and boundary spacing.

The pricking procedure is somewhat messy and painful, particularly if the patient has to repeat the procedure several times during the day. Diabetic children, in particular, are often reluctant to undergo regular blood sugar testing. Some patients tend to be squeamish at the sight of blood, particularly when the blood is their own. As a result, compliance with the recommended testing regime can be difficult to attain because, patients often forego the messiness and pain associated with this invasive procedure, thereby leading to over-dosing or under-dosing of insulin, which can lead to (sometimes serious) complications.

Also, some very old and clumsy individuals find the finger pricking and blood withdrawal procedure difficult to perform, which can, again, lead to the measurement not taking place and associated complications.

A further group of individuals who may forego testing is teenagers who find the procedure inconvenient or socially unacceptable, i.e. they are embarrassed to carry out the test in front of their friends or social acquaintances.

A further drawback with this procedure is that the pricking technique is generally accomplished with the aid of a needle, which should be sterile before use, although it is often the case that patients, through inadvertence or neglect, fail to sterilise the needle, thereby leading to the risk of infection, and, even in the case of a sterilised needle, a wound is created which may become infected.

An additional inconvenience associated with the finger pricking and urine sampling techniques and methods is that they require testing supplies such as collection vessels (containers or receptacles), syringes, and test kits. Many of these supplies are disposable and, therefore special methods of disposal are required.

A need therefore exists for a solution to one or more of the above problems, and/or an alternative to the traditional finger-prick test.

Another invasive technique involves using implantable medical devices to measure cardiac signals. In one such invention, the blood-glucose levels are determined based on T-wave amplitude and the QT-interval. Once the blood-glucose level has been detected, the implanted device compares the blood-glucose level against upper and lower acceptable bounds and appropriate warning signals are generated when the levels fall outside these bounds.

The disadvantage of this method is that the instrument has to be inserted inside the human body and so a complex medical procedure may need to be performed. Also, the patient would need to be admitted to hospital and may need to stay for a few days. Additionally, this device would be classified as a "class III" medical device because it is inserted inside the body. A class III medical device is categorised is a high-risk device and would need to go through stringent testing and validation procedures before being granted approval by the medical devices regulatory bodies to enable it to be put into regular use.

Clearly, implanted devices are generally undesirable and a need therefore exists for an alternative to this system.

It has been widely proposed to use a wearable device to carry out continuous or periodic measurements of the concentration of a target substance in the blood. Wearable devices include such items as devices that are worn around the neck (necklace-type devices); that are worn around the wrist or ankle (watch-like devices). etc. However, where the measurement of the target substance involves a complex or highly-sensitive measurement technique, for example, an RF measurement technique, such devices need to be largely, or completely, immune to extraneous variables, such as the location/fit of the sensor during the course of a test procedure.

For example, a watch-type device might be worn tightly by some users, or loosely be others. Where a watch-type device is worn loosely, this can create number of significant variables, such as the location of the device (where it is positioned relative to the user's anatomy) during a test. A loosely-fitted watch-type device may be located further up or down the wrist at different times; or on top, to the side or underneath the wrist at different times—and this variation will inevitably affect the RF properties of the test at that time.

Second, the contact pressure between the antenna (in the case of an RF-based test) will have a significant effect on the results of the RF-based test procedure. A higher contact pressure is likely to result in better RF coupling between the antenna(s) and the user's skin; as well as (where the skin is pressed-in/deformed slightly, a larger contact area too—compared with a similar test undertaken with a lower contact pressure.

Third, the user's anatomical dimensions/measurements need to be taken into account to avoid discrepancies between identical test carried out on otherwise similar users, but with different wrist diameters, for example. This consideration is of particular concern where transmission or reflection RF measurements are to be used.

For example, where an RF signal is to be transmitted through a user's wrist and detected by a receiver antenna located on the opposite side of the wrist, there is a need for a consistent and reproducible alignment between the transmit and receive antennas from one use to the next. If the transmit and receive antennas are not consistently related to one another dimensionally, then there is a possibility that the transmitted RF signal may "miss" the receive antenna and not be detected.

Likewise, where an RF signal is to be transmitted into a user's wrist and reflected back off an RF reflector located on the opposite side of the wrist, there is a need for a consistent and reproducible alignment between the transmit/receive antenna(s) on one side of the wrist, relative to the RF reflector located on the other side of the wrist. If the transmit/receive antenna(s) are not consistently related to the RF reflector dimensionally, then there is a possibility that the RF signal may "miss" the RF reflector and not be detected by the receive antenna.

A need therefore exists for a solution to one of more of the above problems and/or an improved and/or alternative wearable RF measurement device for testing the concentration of a target substance in patient's blood.

Our own earlier patent, EP1949084 [Orsus Medical Ltd, WO2007/003955, published 11 Jan. 2007] describes a non-invasive measurement technique for determining a concentration of glucose in blood. This patent describes an RF measurement technique in which a transmitted and/or reflected RF signal, that has been modified by a biological tissue structure, is analysed. Variations in the amplitude and phase of the detected signal (compared with the outputted signal) are correlated to blood sugar concentration, thereby yielding a result that is indicative of the blood sugar concentration. This early work provides a foundation upon which the present invention builds.

The scientific literature also is replete with studies apparently showing a strong correlation between the RF properties of blood and its sugar concentration. Such studies are based on in-vitro testing where a sample of blood is extracted from the body of a patient and tested in isolation, i.e. a droplet of blood is placed onto an RF antenna and then analysed. In the case of in-vitro testing, the correlation between blood sugar concentration and the RF properties of the blood sample under test has been found to be quite strong, but this correlation has, unfortunately, been found only to hold true for an individual patient and or for in vitro blood testing- and cannot be generalised for populations or for in vitro testing.

In other words, it is the variation in RF properties of blood, from person-to-person, which has hampered the development and commercialisation of non-invasive blood sugar testing apparatus for the simple reason that the precise relationship (the equation, so to speak) between the blood sugar concentration and the RF properties (e.g. attenuation, phase shift) seems to be unique to each individual patient, and so there is no single correspondence that can be used reliably across populations of patients. This person-to-person variation could be attributable to different patients having different blood properties (e.g. red cell count, white cell count, blood group, cholesterol level, disease, etc.) some or all of which may inevitably vary the RF properties of one individual's blood relative to another individual's.

In addition, even taking into account the disclosure of our own earlier patent (EP1949084), there are other factors that come into play simply because when testing in-vivo (as opposed to in-vitro), there is a complex biological structure involved, which varies tremendously from one patient to the next. Even taking a reasonably "standard" anatomical part (e.g. an ear lobe), there are huge (percentage) variations in dimensions, fat content, skin thickness, flood flow etc., which all have a large effect on the RF properties of the "biological tissue structure", and so any variations in the RF properties cannot easily be attributed to variations in blood sugar concentration (the target substance) where there are so many other factors that can, and do, affect the readings obtained. These variations are described in detail our own earlier patent (EP1949084).

Other known testing devices or techniques are described in the following published patent applications: US 2009/275814 A1 [WATANABE SHINSUKE [JP] ET AL, 5 Nov. 2009]; U.S. Pat. No. 5,508,203 A [FULLER MILTON E [US] ET AL, 16 Apr. 1996], US 2004/147819 A1 [CADUFF ANDREAS [CH] ET AL, 29 Jul. 2004]; GB 1 193 577 A [POLSKA AKADEMIA NAUK ZAKLAD [PL], 3 Jun. 1970]; EP 2 168 518 A2 [VIVANT MEDICAL INC [US], 31 Mar. 2010]; U.S. Pat. No. 5,661,404 A [YANAGAWA KOICHI [JP] ET AL, 26 Aug. 1997]; US 2007/029989 A1 [HARUTA MASATO [JP] ET AL, 8 Feb. 2007]; US 2015/112170 A1 [AMERSON III ROBERT LEE [US] ET AL, 23 Apr. 2015]; US 2013/085356 A1 [SCHLOTTAU FRISO [US] ET AL, 4 Apr. 2013]; US 2013/289375 A1 [FISCHER GEORG [DE], 31 Oct. 2013]; WO 2014/207733 A1 [SENSIBLE MEDICAL INNOVATIONS LTD [IL], 31 Dec. 2014]; US2013225960 [PORCH, 29 Aug. 2013]; and US2014/378812 [SAROKA, 25 Dec. 2014].

A need therefore exists for a solution, which permits reliable, non-invasive, in-vivo testing of a target substance (e.g. sugar) in blood, which provides a generalise solution that can be applied to populations, rather than having to be "calibrated" to individual patient's "variables".

Various aspects of the invention are set forth in the appended claims.

In summary, the present invention is, or relates to, a non-invasive testing apparatus for determining a concentration of a target substance, such as blood sugar, blood alcohol, cholesterol, etc.) in a patient's blood. The apparatus and method involve applying an output RF signal to the skin of a patient via an antenna, and measuring the amplitude and phase of a response signal, which is a function of the output RF signal modified by an interaction with the patient's blood. The invention takes measurements at different output RF frequencies, and plots the response as a function of frequency. The invention is essentially characterised by deriving various derived parameters from the shape of the resulting plots, namely any or more of: a resonance frequency shift; a Q factor of the resonance; a group delay; a phase shift; an amplitude variation; a shape factor of the plot; and a gradient of the plot at different frequencies. The invention utilises models of the derived parameters as a function of concentration of the target substance in blood to arrive at a determination of the latter. Also disclosed herein is a novel circuit for obtaining the amplitude and phase measurements, a calibration device, and various improvements relating to wearable non-invasive testing apparatus.

According to an aspect of the invention, there is provided a non-invasive testing apparatus for determining a concentration of a target substance in a patient's blood, the non-invasive testing apparatus comprising: an RF signal generator adapted, in use, to output an output RF signal; a processor; and at least one antenna operatively coupled, in use, to patient's blood, the or at least one antenna being operatively connected to the RF signal generator and the processor, characterised by the processor being adapted, in use, to: measure a response signal via at least one of the antennas, the response signal being a function of the output RF signal modified by an interaction with the patient's blood, measure the amplitude and phase of the response signal at a plurality of output RF signal frequencies; plot the measured amplitude and phase of the response signal as a function of output RF signal frequencies; using the plot, determine any one or more derived parameters of the response signal from the group comprising: a resonance frequency shift; a Q factor of the resonance; a group delay; a phase shift; an amplitude variation; a shape factor of the plot; and a gradient of the plot at different frequencies; compare any one or more of the derived parameters with a model of the respective derived parameters as a function of concentration of the target substance in blood; and to determine a concentration of the target substance in the patient's blood based on a correlation between the derived parameter or parameters and the corresponding values of concentration of the target substance in the patient's blood in the model.

In contrast to the prior art, the invention, when attempting to determine what the concentration of the target substance is, is concerned principally with derived parameters, rather than the absolute values obtained from the test. The reason for this is that absolute values have been found to vary from patient to patient, or over time—even for the same patient, whereas derived parameters, which are based on the shape of the plot have been found to yield more reliable results. The reason for this is that although the location or scaling of the plot of amplitude/phase vs frequency may shift from test to test, distortion of the plot, that is to say, normalised, relative movements of points of interest in the plots appear to be consistent with their respective models of derived parameters vs target substance concentration from patient to patient and over time. Thus, the invention is capable, in certain embodiments, of providing an accurate test result independently of the patient's physiology and/or the time of testing. This discovery, and the practical application of this discovery in the invention, represents a leap forward in the field of non-invasive blood testing.

In order to improve the robustness of the test, the processor is suitably adapted to: determine a plurality of derived parameters; compare the plurality of derived parameters with respective models of the respective derived parameters as a function of concentration of the target substance in blood; to determine, for each derived parameter, a concentration of the target substance in the patient's blood based on a correlation between the respective derived parameter and the corresponding values of concentration of the target substance in the patient's blood in the respective model; and to apply a statistical model to the resulting determined concentrations of the target substance in the patient's blood based on each derived parameter to arrive at a single, overall determined concentration of the target substance in the patient's blood. This results, in effect, in a "weighted average" or a "best fit" overall result, which can be more reliable and/or robust than relying on a single result from a single derived parameter.

The model can take various forms, although it will be appreciated that the or each model could comprise a lookup table of derived parameters and their corresponding concentrations of the target substance in the patient's blood, and wherein the processor is adapted to identify the closest match to data in the lookup table or to interpolate between data in the lookup table to arrive at a determined concentration of the target substance in the patient's blood. Additionally or alternatively, the or each model could comprise an equation defining a relationship between a derived parameter and concentration of the target substance in the patient's blood, and wherein the processor is adapted to use the derived parameter as the argument of the equation to yield the value being the concentration of the target substance in the patient's blood.

Unlike the prior art, and even our own earlier patent (EP1949084), the invention considers the RF properties holistically, rather than attempting to fit certain measured parameters to a particular equation. For example, in EP1949084, the amplitude and phase of a response signal is plotted as a function of frequency, and the position and amplitude of the observed resonances are correlated with a known, previously-determined, relationship between blood sugar concentration and amplitude; and blood sugar concentration and phase. The measured data points are effectively mapped onto the model to yield a test result being an indication of the blood sugar concentration. However accurate this measurement may be for an individual patient, it still requires some form of "standard" for that patient, which is derived by taking, for example, a series of finger-prick tests beforehand to determine the relationship between blood sugar concentration and amplitude, and/or blood sugar concentration and phase for that individual.

The invention, by contrast, does more than just obtain a series of readings of amplitude and phase at different frequencies: it considers the overall shape of the measured relationship between input frequency and the amplitude of a response signal and/or the input frequency and the phase of a response signal. By doing so, the measured relationships can be more subtly analysed and more reliably fitted to a model, from which the blood sugar concentration can be derived.

According to an aspect of the invention, there is provided a non-invasive testing device comprising apparatus comprising a main body comprising at least one antenna operatively coupled, in use, to the skin of a patient; and a housing comprising at least one receiver antenna and/or reflector also operatively coupled, in use, to the skin of a patient; the housing being located, in use, on an opposite side of the patient's anatomy to the main body; an adjustable strap connecting the main body to the housing, wherein the strap is formed as a pulley belt affixed at one end to the main body or housing, which is wound around respective rollers of the main body and the housing, and which has a free end, wherein the pulley belt and rollers are configured to centralise the housing relative to the main body such that pulling on the free end of the strap reduces the distance between the main body and the housing, whilst maintaining a substantially constant alignment between the main body and the housing.

Suitably, the substantially constant alignment between the main body and the housing is such that a line normal to a centre of the antenna is maintained in a substantially constant relationship to a line normal to a centre of the receiver antenna and/or reflector. Preferably, the line normal to the centre of the antenna is maintained in alignment with the line normal to the centre of the receiver antenna and/or reflector.

An advantage of this configuration, in certain embodiments, is that the strap self-centralises the main body and/or the housing on the patient's body, thereby ensuring, or at least encouraging, a consistent measurement geometry each time a measurement of the target substance is carried out. By aligning the housing and main body, a transmitted signal can reproducibly be sent from the main body to the housing, and/or reflected off the RF reflector back to the main body, which improves the reproducibility of the test.

Suitably, the strap is manufactured from a flexible material, such as an elastomer like silicone rubber. Suitably, the main body, housing and strap is/are manufactured of hypoallergenic materials, such as silicone rubber, which is latex-free; plastics; and/or metals that are low in nickel or other materials that are known to cause irritation and/or allergic reactions.

Suitably, the pulleys are rollers that are rotatably affixed to the main body and housing. The strap, which is typically a band, can pass around the pulleys to achieve the objects of the invention. In one embodiment, the strap is anchored at one end to the main body, and passes around a user's wrist or other body part to a first roller located to one side of the housing. Then, the strap folds back on itself and passes around the same side of the user's wrist or body part back to the main body. It then crosses over and extends around the opposite side of the user's wrist or body part to a second roller located on an opposite side of the housing. The free end of the strap can then be secured, or it can pass back around the same side of the user's wrist to the main body where is secured. The aforementioned configuration thus provides two (but critically an equal number of) strap lengths on either side of the user's wrist, such that pulling on the free end of the strap causes equal movement of the housing relative to the main body. This usefully keeps the strap lengths on either side of the user's wrist or body part substantially equal, or equal, thus self-centralising the housing and main body.

Another aspect of the invention provides a non-invasive testing device comprising apparatus comprising a main body comprising at least one antenna having a front surface operatively coupled, in use, to the skin of a patient and an adjustable strap connected to the main body and extending, in use, around a part of the patient's body to retain the antenna adjacent the patient's skin, the non-invasive testing device further comprising: an air bladder, and means for inflating the air bladder to cause the front surface of the antenna to press against the patient's skin with a predetermined force.

Suitably, the means for inflating the bladder inflates the air bladder to a predetermined air pressure, which in-turn causes the front surface of the antenna to press against the patient's skin with a predetermined force. By ensuring that the front surface of the antenna is pressed against the patient's skin with the same predetermined force each time a test is carried out, the reproducibility of the test can be improved.

The means for inflating the air bladder suitably comprises a pump, which may be an electric pump. However, for convenience, and so as to reduce the need for battery power, the means for inflating the air bladder is preferably a manual pump, such as a compressible bladder with a one-way valve, which can be depressed once, or several times, to inflate the air bladder.

Means is suitably provided for causing the front surface of the antenna to press against the patient's skin with a predetermined force, which means may be a pressure-relief valve interposed between the pump and the air bladder. Such a configuration, by setting the pressure-relief valve to a certain pressure setting, can ensure that the air bladder is not over-inflated. Means, for example, an air pressure sensor, may be provided to ensure that the pump is used/operated until the air pressure within the air bladder reaches at least a predetermined air pressure that ensures that the required predetermined force is achieved.

By using an air bladder, the pressure within it can be hydrostatic, which suitably ensures that an even pressure is applied across the surface of the antenna.

Suitably, the air bladder is interposed between the main body and a rear surface of the antenna.

Suitably, the at least one antenna is operatively connected to a driver and a processor, wherein, in use: the or each; the driver is adapted, in use, to output an output signal via at least one of the antennas; and wherein the processor is adapted, in use, to measure a response signal via at least one of the antennas, the response signal being a function of the output signal modified by an interaction with patient's blood, characterised by the processor being adapted to analyse the response signal and to determine from the analysis, a concentration of a target substance in the patient's blood.

According to another aspect of the invention, there is provided a non-invasive testing apparatus comprising at least one antenna operatively connected to a driver and a processor, wherein, in use: the or each antenna is operatively coupled to the skin of a patient; the driver is adapted, in use, to output an output signal via at least one of the antennas; and wherein the processor is adapted, in use, to measure a response signal via at least one of the antennas, the response signal being a function of the output signal modified by an interaction with patient's blood, characterised by the processor being adapted to analyse the response signal and to determine from the analysis, a concentration of a target substance in the patient's blood.

Suitably, the at least one antenna is operatively coupled to the skin of a patient, and hence to the patient's blood.

According to another aspect of the invention, there is provided a non-invasive testing method comprising the steps of: using a driver, outputting an output signal via at least one antenna to the skin of a patient; measuring, using a processor, a response signal via at least one antennas, the response signal being a function of the output signal modified by an interaction with patient's blood; the method being characterised by the step of analysing the response signal and determining from the analysis, a concentration of a target substance in the patient's blood.

In certain embodiments of the invention, the non-invasive testing apparatus comprises an antenna via which the output signal is sent, and the response signal is received.

In other embodiments of the invention, the non-invasive testing apparatus comprises a first antenna via which the output signal is sent, and a second antenna via which the response signal is received.

The response signal can be either or both of: a transmitted signal (i.e. in which the first and second antennas are placed on opposite sides of a target body part, such as an ear lobe) and/or a reflected signal (i.e. in which the antenna, or the first and second antennas are placed on one side of a body part, and the output signal is reflected off a structure within the body part back to the antenna, or second antenna). In the case of a transmitted signal, the first and second antennas can be placed side-by-side on one side of the target body part, but the gain (the sensitivity of the antenna in a certain direction, as indicated schematically by the lobes in FIG. 4) of the first and second antennas is suitably configured (by virtue of the antenna design) to be directional, such that the output signal is directed towards the second antenna, and such that the gain (directionality, or direction of increased sensitivity) of the second antenna is biased/angled towards the direction of the first antenna.

The ability to use one or more antennas on one side of a body part is particularly advantageous for many reasons, chief of which being removing variables such as the dimensions of the body part.

The driver suitably comprises a signal driver adapted to output signals in the 8 GHz to 30 GHz range. In one embodiment of the invention, the driver is adapted to output a scanning output signal. In other embodiments of the invention, the driver is adapted to output a series of output signals at discrete frequencies or frequency ranges. By outputting output signals over a continuous range of frequencies, or in frequency steps, it is possible to conduct spectroscopic analysis of the patient's blood.

Additionally or alternatively, the driver is suitably configured to output a short-duration (typically 1 to 10 ms) burst signal. In such a situation, the processor is suitably adapted to transpose response signal from the time domain to the frequency domain (for example, using a Z-transform) to obtain a frequency spectrum. Such a configuration can greatly shorten the time taken to perform an analysis of the patient's blood.

Additionally or alternatively, the apparatus may comprise a plurality of frequency-matched antennas, that is to say, antennas tuned to particular bandwidths. In such a situation, the driver may be configured to output a corresponding plurality of narrow-bandwidth output signals to each of the frequency-matched antennas. Such a configuration provides a number of distinct advantages: by frequency-matching the antennas to relatively narrow bandwidths, an improved signal resolution and responsiveness can be obtained; and it is possible to multiplex the signals, such that a quasi-spectrum is obtained in much quicker time, that is to say, by simultaneously outputting, and receiving at, a plurality of discrete bandwidths.

The processor can be integrated into the non-invasive testing apparatus, or it can be physically or logically separate from it. In certain embodiments, the invention comprises an I/O interface that operatively connects the driver and processor to a supplementary processing unit, which can be located, for example, in a dedicated processing unit, smartphone, tablet PC or PC type device. By such means, the complex data processing functions can be carried out in firmware, or an application, of a higher-powered device separate from the main body of the non-invasive testing apparatus itself. It will be appreciated that such a configuration may also enable the supplementary processing unit to be located on a cloud-based server, for example, via the interne, thus enabling a number of users (e.g. the patient, a medical practitioner, relatives and so on) to access the test results in real-time or subsequently.

According to the invention, the or each antenna is operatively coupled to the skin of a patient. Suitably, this can be accomplished by the or each antenna comprising a flat, planar, or patch antenna, which can be placed in direct contact with the user's skin. Additionally or alternatively, a coupling medium may be interposed between the or each antenna and the patient's skin, for example, a gel or cream applied to the skin or antenna prior to carrying out a test. In certain embodiments of the invention, a superstrate material encapsulates the antennae, which material provides a match with the skin.

According to the invention, and further to the foregoing, the processor is adapted, in use, to measure a response signal via at least one of the antennas. The processor may be configured to record the response signal and pass it to a supplementary processor, such as described above. Additionally or alternatively, the processor of the non-invasive testing apparatus itself may be adapted to analyse the response signal and to determine from the analysis, a concentration of a target substance in the patient's blood.

The non-invasive testing apparatus suitably comprises one or more human interface devices (HIDs), such as a start/stop button for initiating and/or terminating a test. The start/stop button, in certain embodiments, may be incorporated into a housing of the non-invasive testing apparatus, for example, as a slide switch interposed between two relatively moveable parts of a housing for the non-invasive testing apparatus. By such means, a user may depress a housing of the non-invasive testing apparatus onto the skin, thereby initiating and/or terminating a test. The HID may additionally comprise indicator means, such as an LED and/or a beeper, to provide feedback to the user, such as "test initiated", "test in progress", "test complete", "test error" etc. It will be appreciated that different combinations of LED colours and flashing sequences, or beep combinations, could be used to signify the different statuses of the non-invasive testing apparatus.

Additionally or alternatively, the HID comprises a display screen, which can be used to display the different non-invasive testing apparatus statuses and/or a test result.

The non-invasive testing apparatus may additionally comprise a memory for storing previous test results, which can be displayed on a display screen of the HID, as desired, but this is an optional, albeit preferred, feature of the invention. Embodiments of the invention may also have the facility to connect directly, or indirectly, via an interface cable to a PC, laptop, tablet device etc., such that the data can be downloaded, e.g. for offline analysis subsequently.

A particular problem that exists in relation to making RF measurements, such as is contemplated by the foregoing embodiment(s) of the invention, is a need for accurate signal generation and signal processing to be able to analyse the results of a test. In particular, when an antenna is used to transmit an RF signal into a sample, and a response detected simultaneously/subsequently, a great deal of signal processing needs to be carried out in order to obtain readings of the parameters of the test sample.

In order to achieve this, it is usually necessary to use a network analyser-type device, which has a sophisticated signal generation component as well as a sophisticated signal processing component. A network analyser is an extremely sensitive device and is generally very costly, which makes it generally unsuitable for use as a portable and/or low-cost device.

Furthermore, a network analyser can be very difficult to configure and can be highly susceptible to physical variables, such as the cable routing and/or configuration etc. when obtaining a result. As a result, it can be extremely difficult to obtain accurate, reproducible, and/or consistent test results in RF-based systems.

Of particular concern, in the context of the invention, is the reproducibility of the test on a given patient from one time to another. One reason for this is the use of fly leads to interconnect the network analyser with the transmit/receive antennas. Even though the fly leads may be well-shielded and efficiently coupled to the antennas, movement of the fly leads during a test procedure can result in errors occurring. Therefore, it is imperative that the test subject/specimen is kept completely still during the test, which can be inconvenient.

More importantly, however, the reproducibility of an RF-based test can be difficult to achieve due to differences in the physical set-up of the system from one test to another. Because it is not possible to precisely reproduce the exact physical configuration of the network analyser and test subject from on test to another (i.e. tests taken at different times, even with the same patient), test results have been found to be error-prone and subject to considerable drift, which may be attributable, in part, to changes in the RF properties of the test subject, but also in terms of the physical set-up during the test.

Unfortunately, it is not easy to differentiate between intrinsic variations (for example changes in the blood sugar level of a test patient) and extrinsic factors (such as differences in the fly lead configuration, RF interference, etc.). This leads RF-based testing being somewhat susceptible to errors and false results.

A need therefore exists for a solution to this problem.

A yet further aspect of the invention provides a circuit comprising: an RF signal generator adapted, in use, to provide an RF signal at its output, the output of the RF signal generator being connected, in use, to an input node, the input node being configured, in use, to split the RF signal into sustainably equal first and second signals, the first signal being connected to a test output via a test specimen, the second signal being connected to a reference output via an adjustable reference circuit, the test and reference outputs being connected, in use, to respective inputs of a comparator, the comparator being adapted in use to output, at a comparator output, a difference between the test output and the reference output, the circuit further comprising a microprocessor comprising: a microprocessor input connected, in use, to the comparator output; and a control output connected, in use, to the reference circuit; wherein the reference circuit comprises a variable attenuator and a variable phase shifter controllable, in use, by the control output of the microprocessor, and wherein the microprocessor is adapted, in use, to: adjust its control output and thereby adjust the amplitude and phase of the reference circuit so as to bring the comparator output to zero, or substantially zero, whereby the adjustable reference circuit is adjusted such that it is an analogue of the test specimen; and to output a data signal indicating the amplitude and phase of the reference circuit where the comparator output is zero, or substantially zero.

By splitting the RF signal at the node into two components at the node, namely: a first component that analyses the specimen, and a second component that goes through a reference circuit, and then by adjusting the reference circuit such that the difference between the test and reference components is zero, the apparatus effectively becomes immune to many of the extrinsic variables of the test. Furthermore, by carrying out the test in this way, the signal generator can be greatly simplified, as can the signal analysis, which can be carried out by the microprocessor instead of by a network analyser-type device.

Suitably, the RF signal generator comprises a stable resonator circuit capable of outputting an RF signal having a substantially constant amplitude, frequency, and phase. The RF signal generator can, in certain embodiments, comprises means for selectively adjusting any one or more of the amplitude, frequency, and phase of the RF signal at its output. Preferably, the RF signal generator is adapted, in use, to continuously adjust (sweep) any one or more of the frequency, amplitude, and phase of the RF signal at its output; or in certain embodiments, to incrementally adjust (step-change) any one or more of the frequency, amplitude, and phase of the RF signal at its output. This greatly simplifies the RF signal generation, compared with the use of a network analyser.

In certain embodiments, the RF signal generator comprises a quartz crystal resonator; or a plurality of quartz crystal resonators, each being configured to output a different frequency, amplitude and/or phase RF signal. Switch means is suitably provided for selectively connecting a selected one of the plurality of quartz crystal resonators to the RF signal generator's output such that the RF signal generator can selectively output an RF signal having a selected frequency, amplitude and/or phase.

Preferably, the effective signal path lengths of the conductors carrying the first and second signals between the input node and the inputs of a comparator are equal or sustainably equal. This configuration reduces any variability based on signal transmission through the apparatus, and hence inherent differences in the outputs of the two signal paths.

In a preferred embodiment of the invention, the first signal is coupled to the test specimen via one or more antennas. The antenna or antennas may be of any suitable configuration, but especially of any configuration as previously and herein described.

In certain embodiments of the invention, the comparator comprises bridge-type circuit, such as a Wheatstone bridge. A bridge circuit provides a relatively simple, analogue means for obtaining a difference between (and optionally a sum of) two signals at its inputs. Bridge circuits are relatively inexpensive, reliable, and simple devices, which is an advantage in a portable device.

The circuit may further comprise an RF demodulator interposed between the comparator output and the microprocessor input and optionally a low-frequency demodulator interposed between the comparator output and the microprocessor input. The demodulator(s) where provided, are suitably adapted to provide a DC signal or PWM signal at the input of the microprocessor, which is proportional to the difference between the first and second signals.

The data signal indicating the amplitude and phase of the reference circuit where the comparator output is zero, or substantially zero is preferably represented on a display device, such as a display screen, an LCD panel, or one or more dials. This display may be numerical, or graphical. Preferably, means is provided for displaying a concentration of the target substance based on the phase and amplitude values required to cause the reference circuit to equal/balance the test circuit.

One or more fly leads may be used to connecting any one or more of: the RF signal generator and the input node; the comparator output and the microprocessor input; and the microprocessor's control output and the reference circuit. The fly lead or fly leads, where provided, may comprises detachable connectors.

Preferably, the reference circuit comprises both coarse and finely adjustable variable attenuators and variable phase shifters. A possible advantage of this configuration is that the coarse adjustments can be set (roughly) to the settings of a previously-carried-out test, such that the variable attenuator and variable phase shifter settings are approximately correct at the start of a subsequent test. This can speed-up the test procedure considerably if, for example, the settings of the variable attenuator and variable phase shifters are approximately correct at the start of a test.

In another possible embodiment of the invention, the transmit and/or receive antennas are incorporated into a self-adhesive plaster-type device, which can be adhered to the patient's skin. The advantage of this configuration is that, provided the plaster-type device is not removed and/or repositioned between tests, the tests will be constantly carried out on the same part of the body, which removes many of the extrinsic variables described herein, which often plague RF and/or non-invasive testing. However, unless the entire test circuit (signal generator, signal processor, display/output) is also to be incorporated into the plaster-type device (which could/would be uneconomic and difficult in practice), then fly-leads are needed to connect the plaster-type device to the RF signal generator and analyser. However, the use of fly leads, as described herein, can be problematic as they tend to introduce difficult-to-quantify and/or variable and/or unquantifiable variables in the signal transmission system—that is to say, the part of the circuit between the RF signal generator and the antenna(s) and/or between the antenna(s) and the signal analyser.

A need therefore exists for a means for determining, and hence factoring-out, variables in the signal transmission system.

Another aspect of the invention therefore provides a calibration apparatus comprising: an antenna connected to a connector having an input connected, in use, to an RF signal generator and/or analyser; and switch means interposed between an output of the connector and the antenna, the switch means having an input connected to output of the connector, a first output connected to the antenna(s), a second output connected to an open circuit, a third output connected to ground, and a fourth output connected to a reference load, wherein the switch means can be actuated to connect the connector to each of the four outputs individually such that, in use, the antenna can be calibrated relative to a signal transmission system connected to the input of the connector.

The switch means can be of any suitable type, such as a relay, mechanical switch, MEMS switch, a transistor, MOSFET, etc. However, preferably, the switch means comprises a solid-state switch, which is advantageous because it has no moving parts and is therefore less likely to alter the calibration due to physical movement, arcing, vibration, power surges etc.

Suitably, the calibration apparatus is incorporated into a clamp-type tester, which can be clamped onto a body part, such as an ear lobe of a patient. The clamp-type tester suitably comprises opposing antennas (a transmit and a receive antenna) and a calibration apparatus is suitably, therefore provided for each of the antennas.

In a preferred embodiment of the invention, the reference load comprises a 50Ω, load.

In order to calibrate the antenna, the switch means can be actuated to cycle an input RF signal to each of its four outputs, namely to the open circuit, shirt-circuit, reference load, and the antenna, and the measured response can be analysed at each of the four switch positions. Then, a calibration algorithm can be applied (such as a calibration matrix) to calibrate the antenna and this factor-out any variables associated with the transmission system. By placing the calibration apparatus immediately before the antenna(s), all of the variables in the transmission system can (in many cases) be accounted for, thus improving the reliability and/or reproducibility of a test procedure.

Where the calibration apparatus is incorporated into a clamp-type tester, as previously described, the switch means may further comprise a fifth output/position, which connects the output of a first connector (associated with a first antenna) to an output of a second connector (associated with a second antenna). This provides a "bypass" or "passthough" signal path, which bypasses both antennas, and thus enables the transmission system to be calibrated independently of the antennas and any test specimen therebetween.

It will be appreciated that the calibration apparatus can be readily miniaturised, and is relatively inexpensive, and so can be incorporated into a disposable plaster-type antenna device, which can be used on a patient.

A plaster-type antenna with a connector could be worn underneath a wrist-watch type device containing an RF signal generator, RF signal analyser and/or display as described herein.

Various embodiments of the invention shall now be described, by way of example only, with reference to the accompanying drawings, in which.

Figure 12:
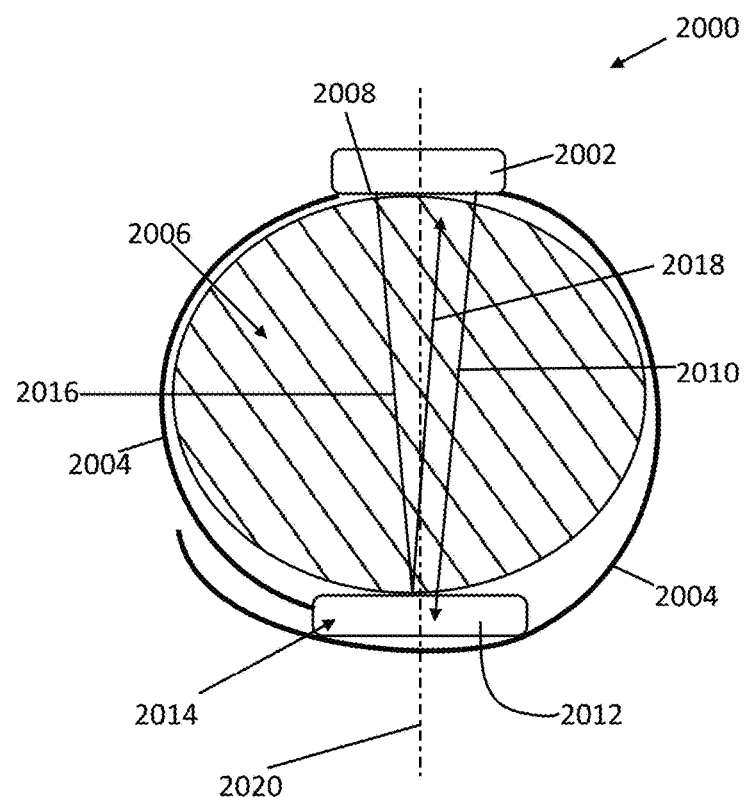
FIG. 12 is a schematic cross-section of a known wearable device adjusted to a first size.
Figure 13:
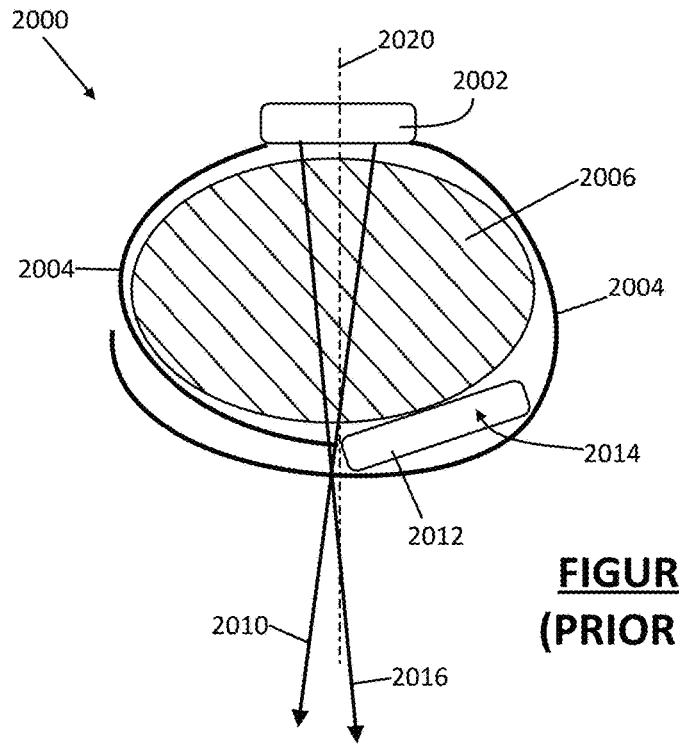
Figure 14:
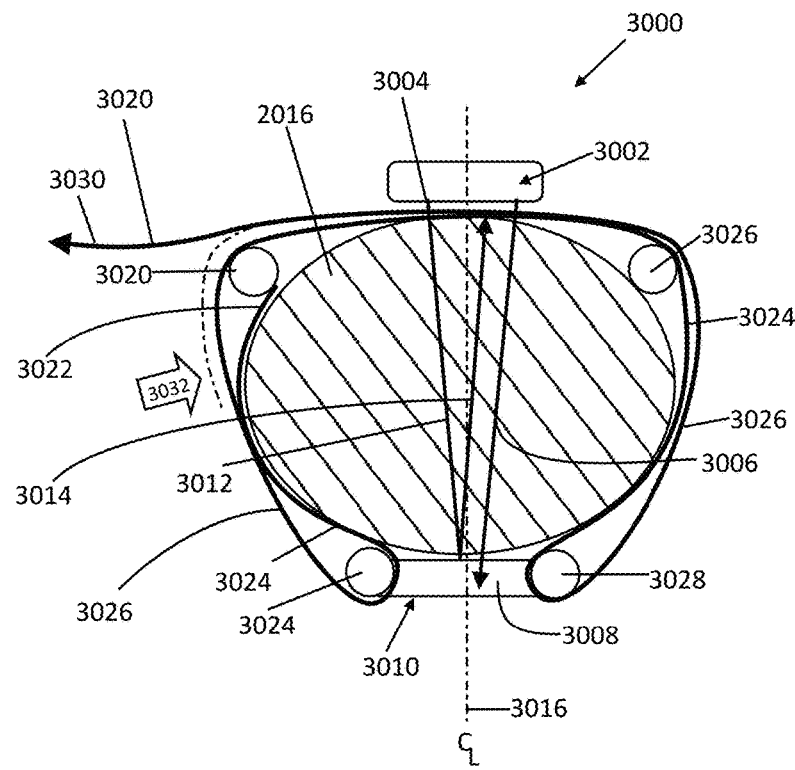
Figure 15:
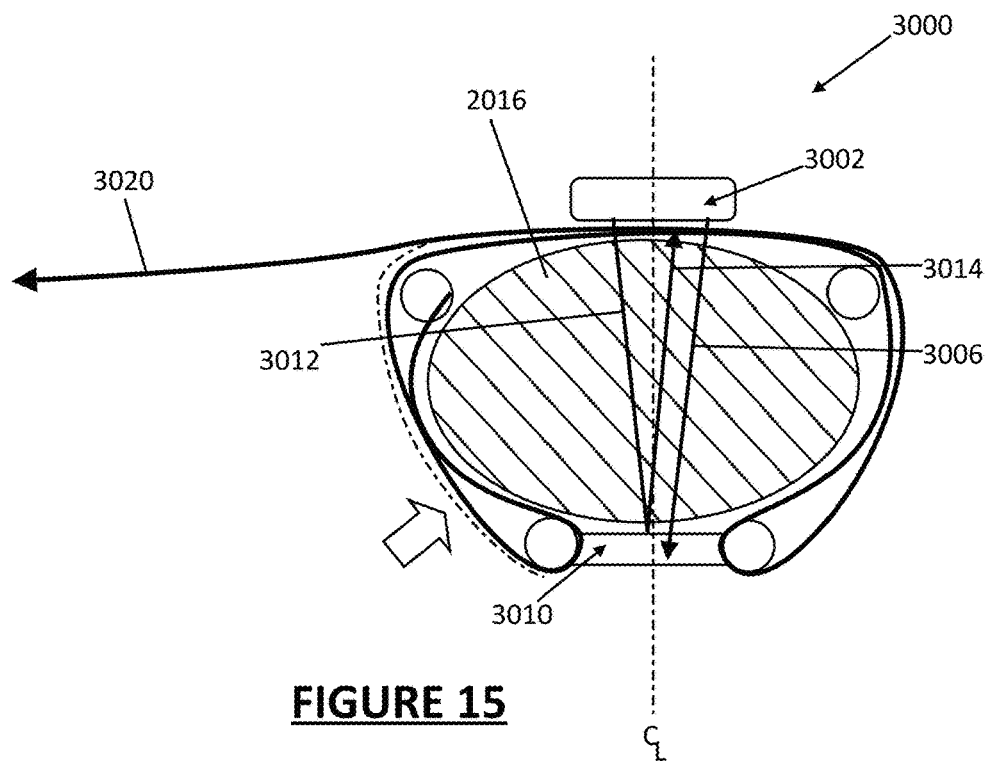
Figure 16:
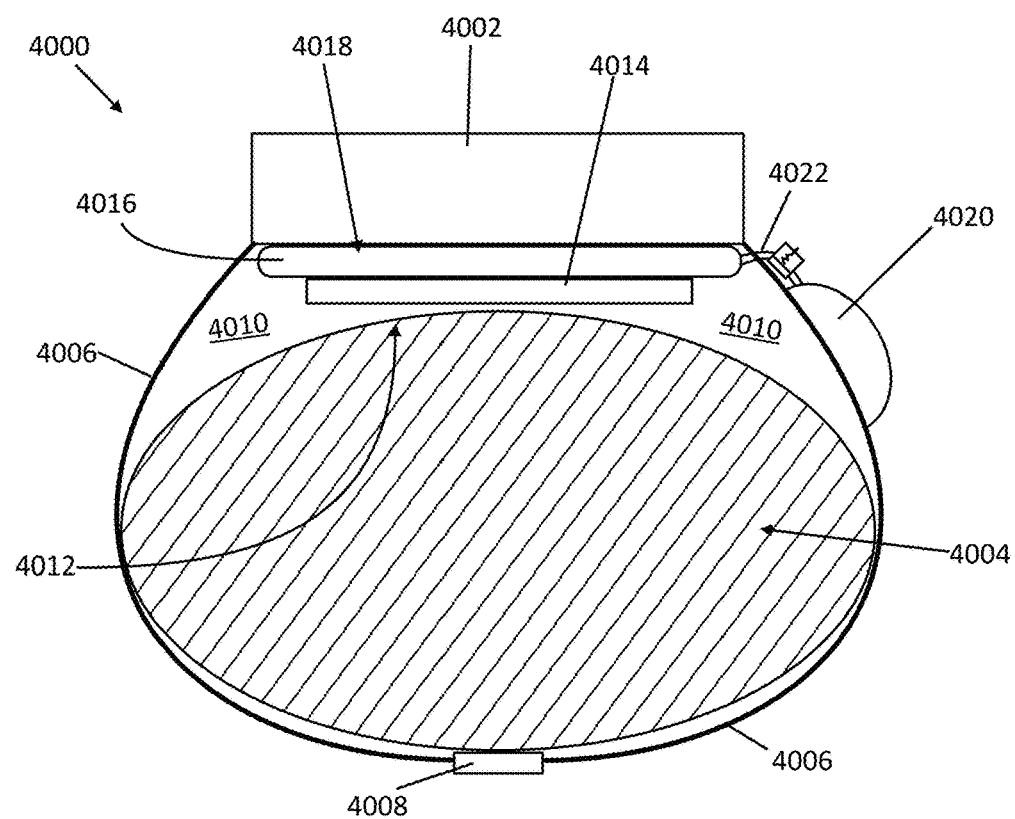
Figure 17:
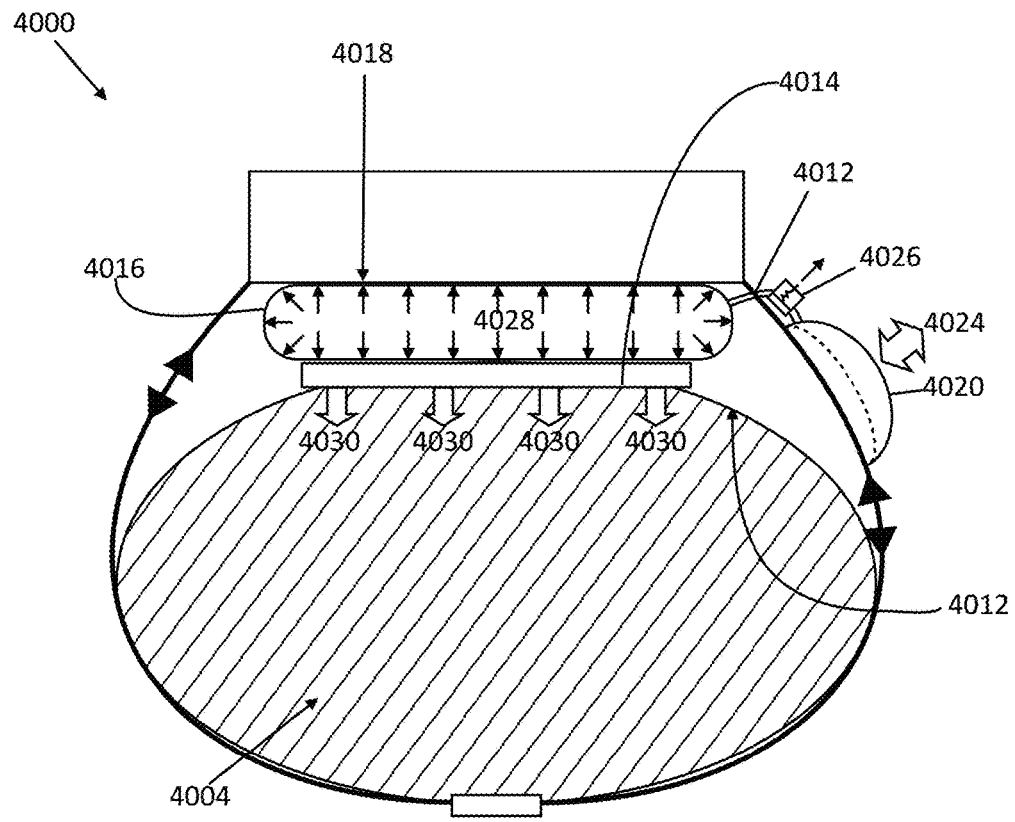
Figure 18:
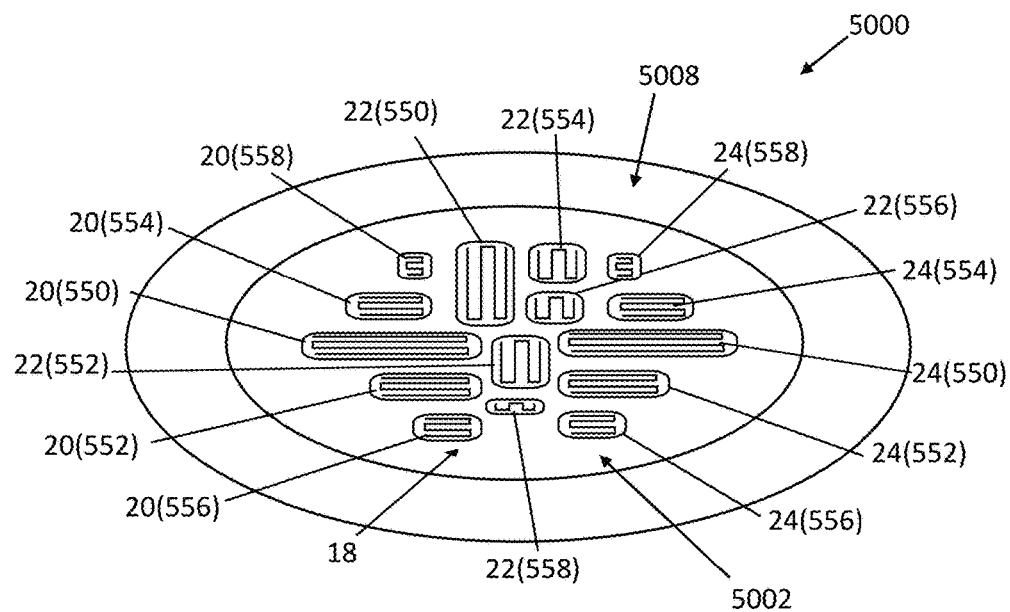
Figure 19:
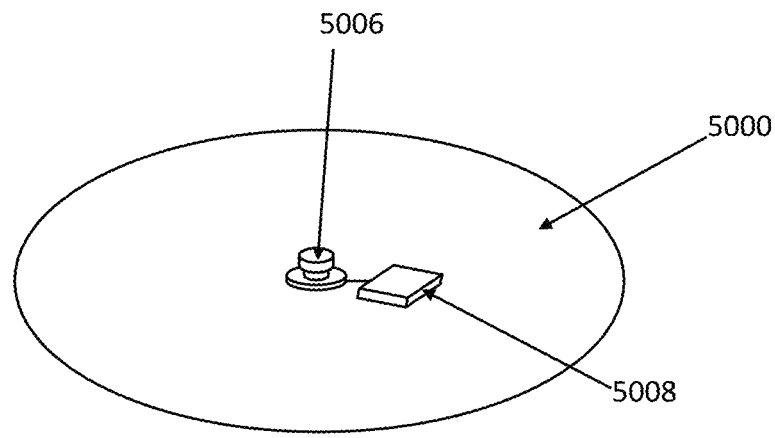
Figure 20:
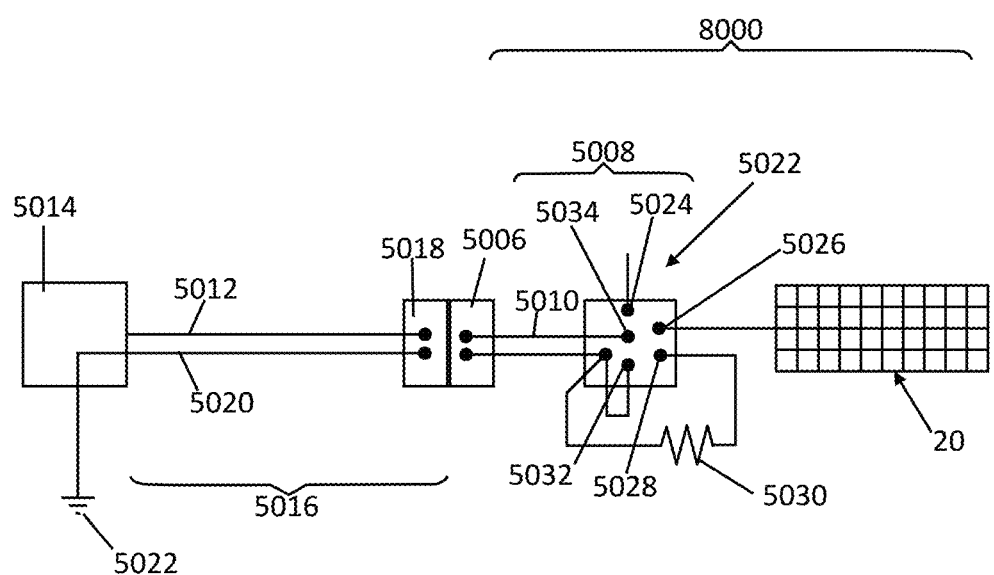
Figures 21, 22:
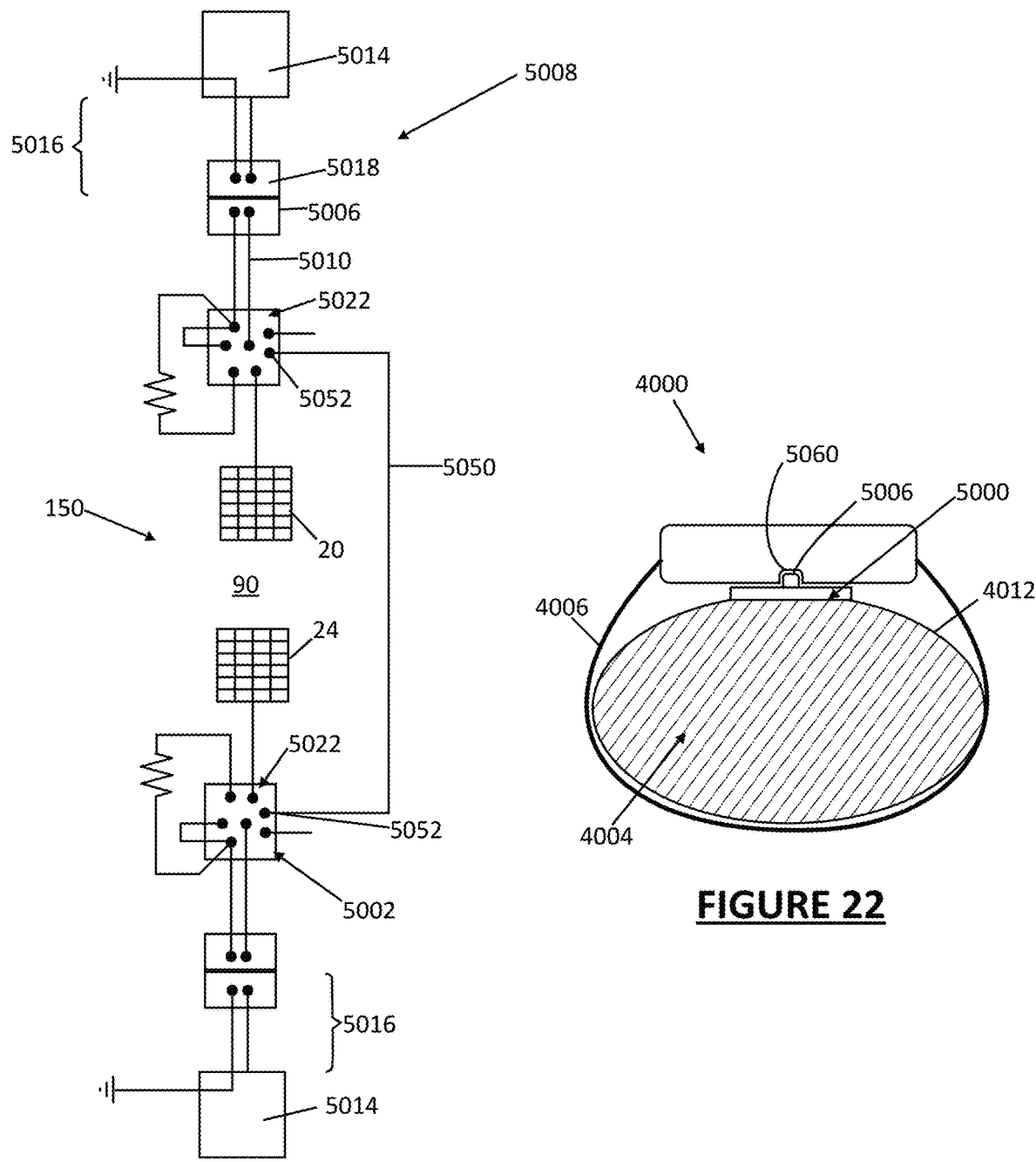

FIG. 13 a schematic cross-section of the known wearable device of FIG. 12 adjusted to a second size;

FIG. 14 is a schematic cross section of an embodiment of a wearable device in accordance with the invention adjusted to a first size;

FIG. 15 is a schematic cross section of the wearable device of FIG. 14 adjusted to a second size;

FIG. 16 is a schematic cross section of another embodiment of a wearable device in accordance with the invention fitted loosely;

FIG. 17 is a schematic cross section of the wearable device of FIG. 17 in an inflated condition ready for use;

FIG. 18 is a perspective underside view of a stick-on antenna patch in accordance with an embodiment of the invention;

FIG. 19 us a perspective top view of the stick-on antenna patch of FIG. 18;

FIG. 20 is a schematic circuit diagram of a first calibration apparatus in accordance with the invention;

FIG. 21 is a schematic circuit diagram of a second calibration apparatus in accordance with the invention; and FIG. 22 is a schematic side view of a test probe suitable for use with the second calibration circuit of FIG. 21.

Figure 1:
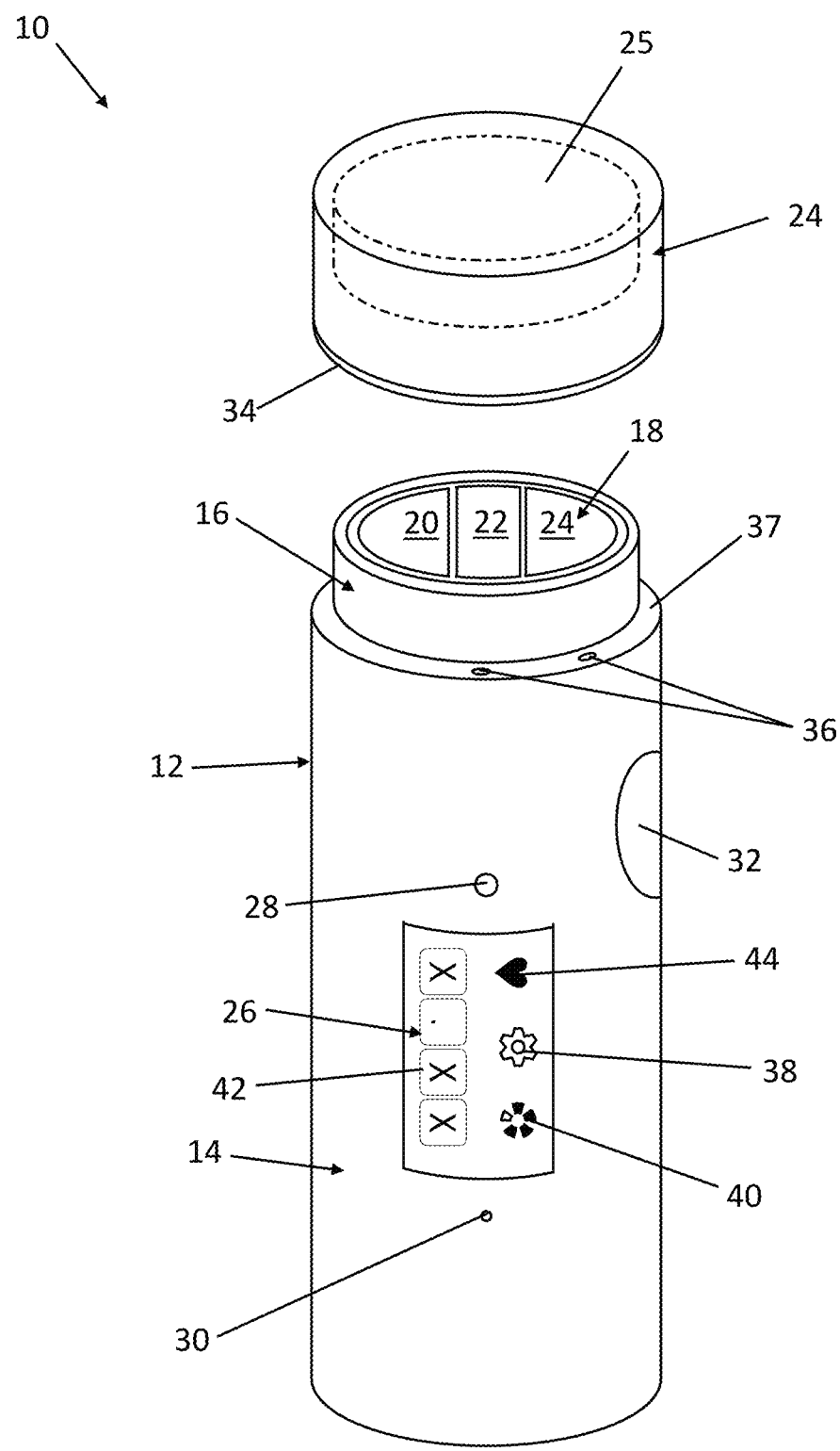
FIG. 1 is a schematic perspective view of an embodiment of a non-invasive testing apparatus in accordance with the invention.
Figure 2:
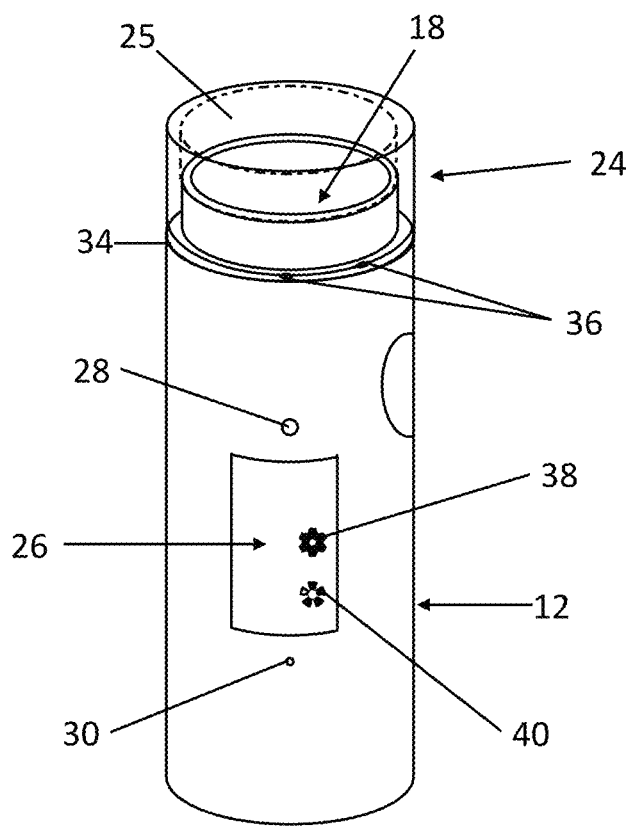
FIG. 2 is a perspective view of the non-invasive testing apparatus of FIG. 1 in a calibration mode.
Figure 3:
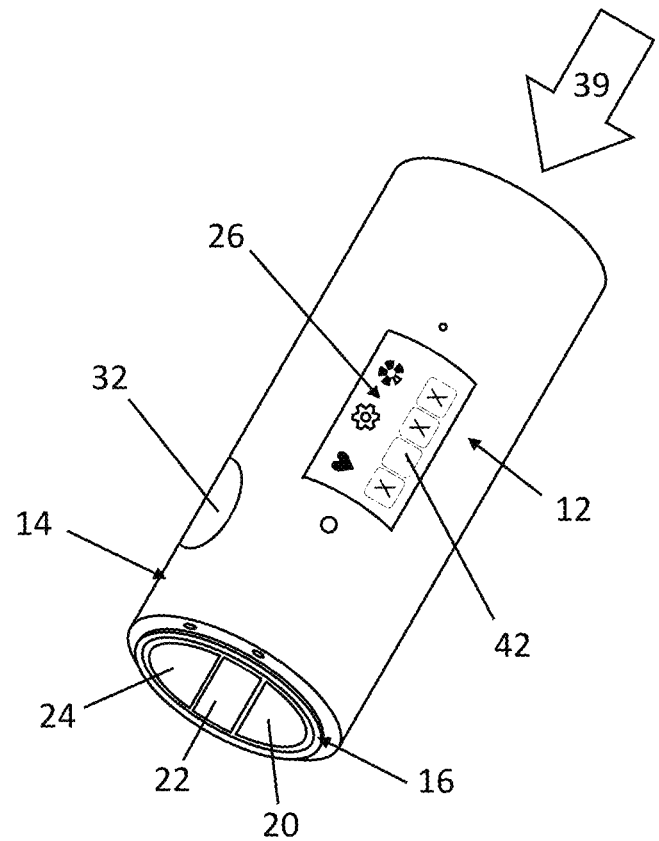
FIG. 3 is a perspective view of the non-invasive testing apparatus of FIG. 1 in use.

Referring to FIGS. 1 to 3 of the drawings, an embodiment of a non-invasive testing apparatus 10 in accordance with the invention comprises a main body portion 12 formed of a first generally cylindrical part 14 and a second generally cylindrical part 16 nested, and slidingly receivable within the first part 14. The second part 16 has a generally planar end surface 18, upon which are disposed three patch antennas 20, 22, 24, which, in use, are placed in contact with the skin of a patent. The non-invasive testing apparatus 10 further comprises an end cap 24 which fits over the second part 16 when the non-invasive testing apparatus 10 is not in use, to protect the patch antennas 20, 22, 24.

The first part 14 of the main body 12 comprises a display screen 26, an LED indicator 28, a beeper 30 and a manual push-button 32, whose functions shall be described below. The main body 12 houses a driver circuit (not shown) and a processor (not shown), which are operatively connected to the patch antennas 20, 22, 24.

To use the non-invasive testing apparatus 10, a patient places the end cap 24 over the second part 16 and presses the push button 32 to start a calibration sequence. The end cap 24 comprises an insert 25, which is formed from any one or more standard materials (preferably three standard materials) having known properties. When the end cap 24 is fitted onto the main body, as shown in FIG. 2, the insert 25 contacts the patch electrodes 20, 22, 24, enabling the driver (not shown) and the processor (not shown) to start a calibration sequence.

The end cap 24 comprises an annular metal rim 34 that forms an electrical connection, when placed onto the main body 12, between a pair of electrodes 36 located on an abutment edge 37 of the first part 14 of the main body 12. Forming a connection between the electrodes 36 signifies to the processor (not shown) that the end cap 24 is correctly seated on the main body 12 with the insert 25 in contact with the patch electrodes 20, 22, 24.

During the calibration sequence, the display screen 26 shows a calibration symbol 38, and a progress indicator 40 counts down the calibration sequence. Once the calibration sequence is complete, the LED 28 illuminates green and the beeper 30 beeps to signify this to the patient.

The end cap 24 can then be removed, and the non-invasive testing apparatus 10 is ready for use.

As shown in FIG. 3 of the drawings, the patient presses 39 the patch electrodes 20, 22, 24 against his/her skin, and the second part 16 of the main body 12 retracts against the action of a spring, into the first part 14. An internal micro switch (not shown) detects when the second part 16 has been fully depressed into the first part 14, thus triggering the start of a test.

At this point, the driver (not shown) sends one or more output signals to one or more of the patch antennas 20, 22, 24, and the processor (not shown) monitors the response(s). The processor (not shown) analyses the responses and calculates a concentration of a target substance (e.g. blood sugar) and indicates this as a numerical value 42 on the display screen 26. During the test, the LED 28 illuminates amber, and during the calculation the LED 28 flashes amber and the progress indicator 40 scrolls. Once a result has been calculated, the LED 28 illuminates green and the beeper 30 beeps to signify this to the patient. A validation symbol 44 can also be shown on the display screen 26 to indicate the confidence of the test, i.e. whether the test should be repeated.

Another useful feature of the non-invasive testing apparatus 10 is that it can also take a pulse reading and display this to the patient during, or after a test.

In the embodiments of FIGS. 1 to 3 described above, there are three patch antennas 20, 22, 24 formed on a surface 18 of the second part 16 of the apparatus 10. A first one of the patch antennas comprises a transmitter antenna 20, which is operatively connected to the driver 80. Meanwhile, a second one of the patch antennas comprises a receive antenna 24, which is operatively connected to the processor 82. The third patch antenna 22 is interposed between the transmit 20 and receive 24 antennas.

Figure 4:
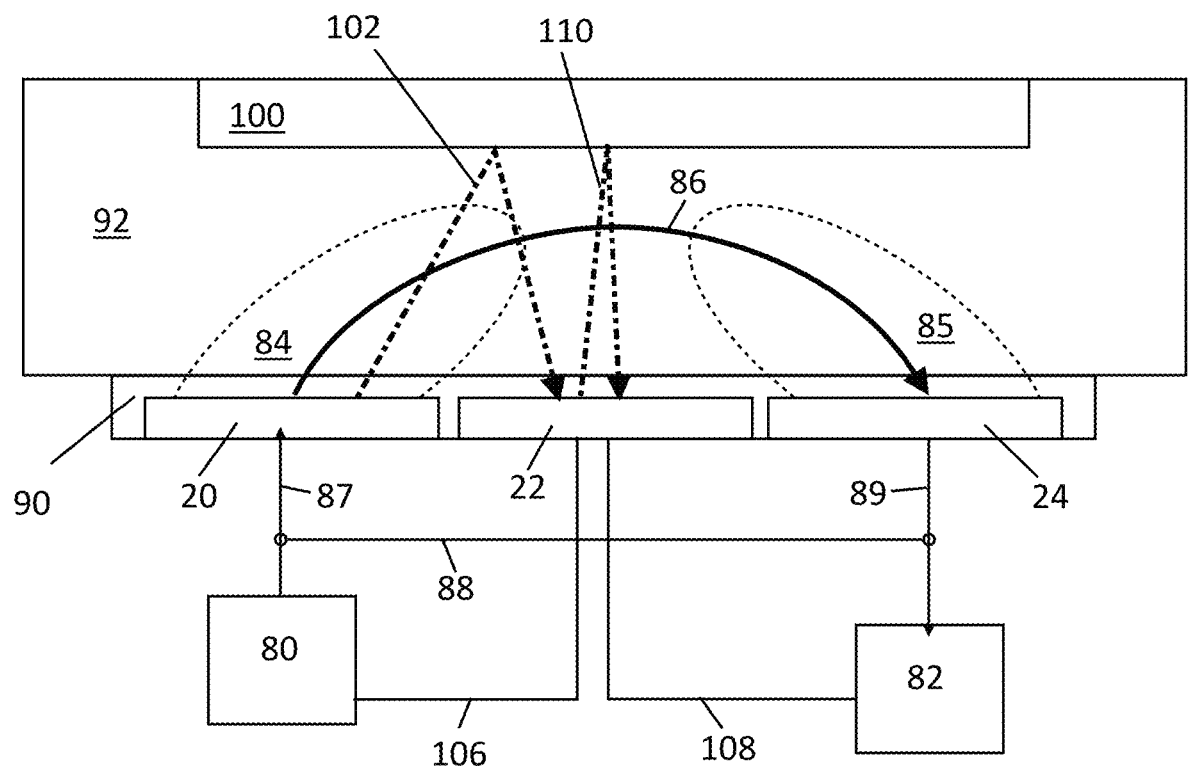
FIG. 4 is a schematic cross-section of FIG. 3 on IV-IV.

Referring now to FIG. 4 of the drawings, it can be seen that the configuration described previously sees the three antennas 20, 22, 24 placed side-by-side and in contact with the skin 92 of a patient. The antennas 20, 22, 24 are encapsulated in a matching material 90, which matches the surface 18 of the second part 16 with the skin 92 of a patient.

The transmit 20 and receive 24 patch antennas are designed so as to have a directional gain, as indicated schematically by the lobes 84, 85 in FIG. 4. In alternative embodiments (not shown), the patch antennas 20, 22, 24 could be angled relative to the surface 18 to obtain a similar effect. Thus, a signal 86 is emitted into the patient's skin from the transmit antenna 20 at an angle, and the gain 85 of the receiver antenna 24 is directed towards the transmitted signal 86 to receive it. Thus, the processor 82 is able to compare 88 the difference between the transmitted signal 87 and the received signal 89 to perform an analysis of the blood within the patient's skin 92.

In certain situations, the skin 92 may comprise subcutaneous structures 100, such as bone, which reflect the transmitted signal. The third antenna 22 is operatively connected to the processor 82, and is configured to pick up signals 102 reflected off such structures 100. The third antenna 22 can, in certain embodiments, serve both as a transmit and as a receive antenna, in which case it is operatively connected 106, 108 to the driver 80 and the processor 82 to analyse reflected signals 110.

Figure 5:
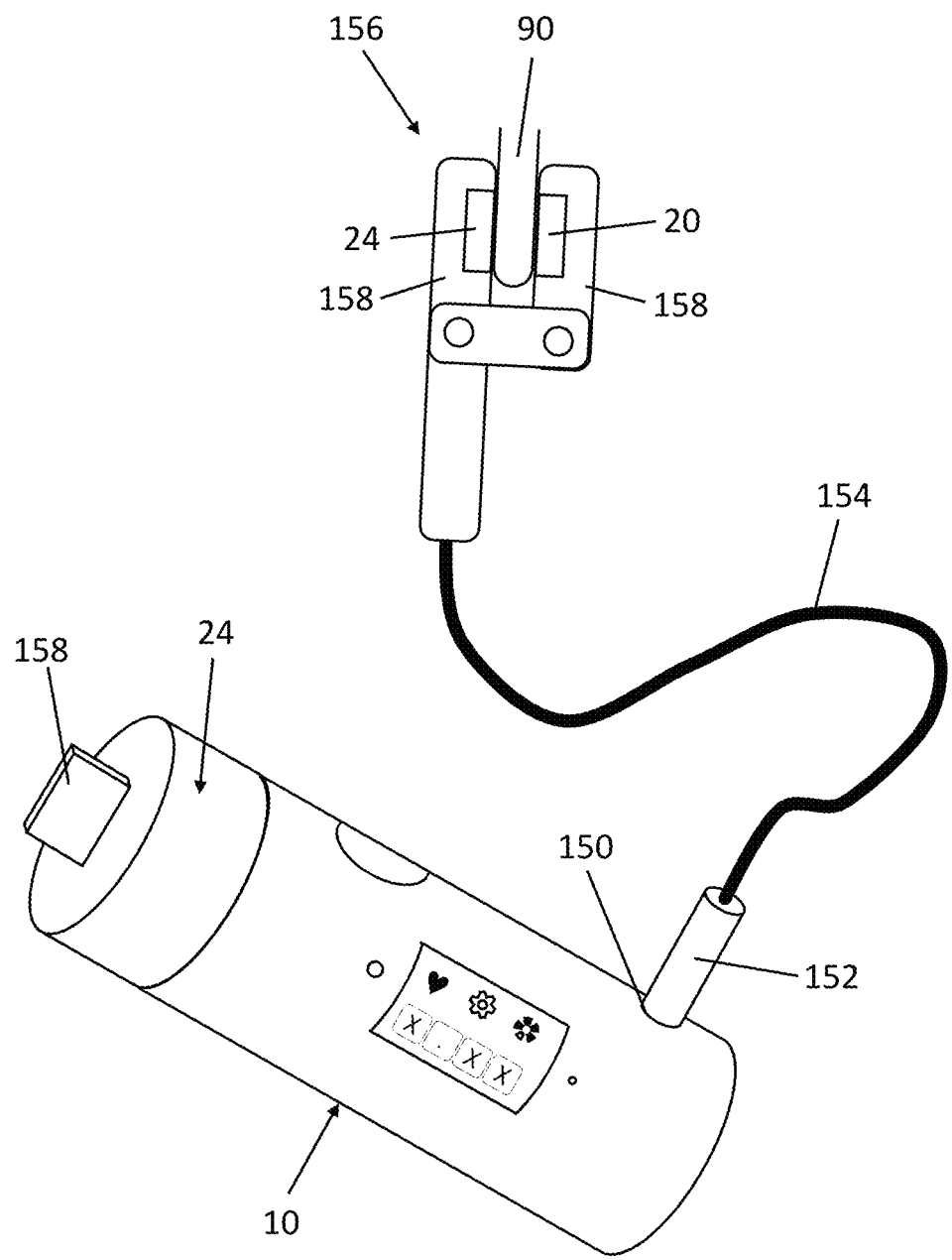
FIG. 5 is a schematic perspective view of a first alternative embodiment of a non-invasive testing apparatus in accordance with the invention.

A further alternative embodiment of the invention is shown in FIG. 5 of the drawings, in which the non-invasive testing apparatus 10 comprises a probe jack 150 into which the plug 152 of a fly lead 154 can be inserted. The fly lead 154 carries at its free end, a clip device 156 comprising opposable pads 158 each comprising a transmit 20 and a receive 24 patch antenna. The clip device 156 can be clipped onto the earlobe, or fingertip, say, of a patient, and the test performed in a manner similar to that previously described.

In this configuration, the device could measure the transmission and reflected characteristics of a part of the body that does not have a natural reflecting internal structure like, but not restricted to bone, or cartilage.

In this example, the clip device 156 can be clipped onto a protrusion 158 manufactured of a calibration material, which protrusion extends from the end cap 24, to enable a calibration sequence to be performed.

Figure 6:
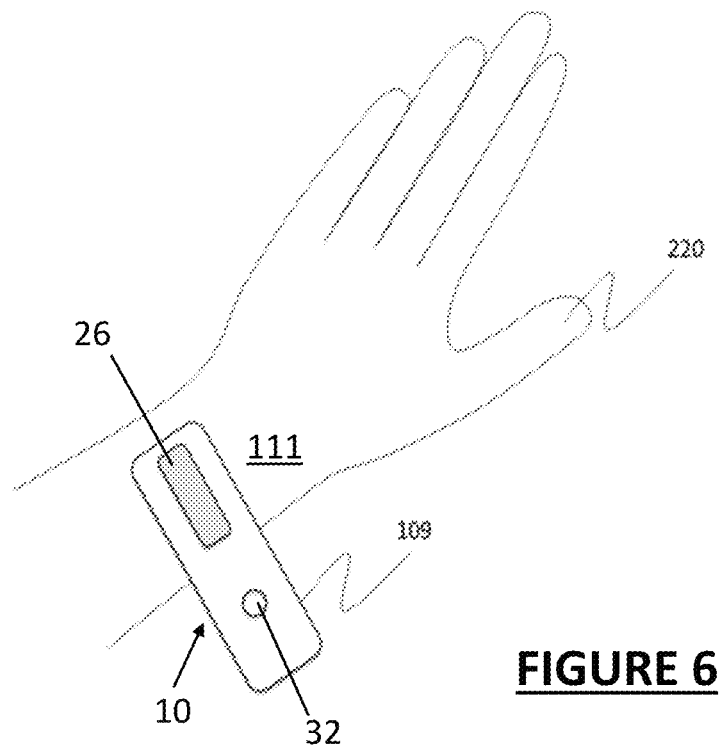
FIG. 6 is a schematic perspective view of a second alternative embodiment of a non-invasive testing apparatus in accordance with the invention.

In a yet further embodiment of the invention, as shown in FIG. 6 of the drawings, the non-invasive testing apparatus 10 is formed as a wand-type device 109, which can be placed, for example, onto the wrist 111 of a user's hand 220. In this embodiment, the directional patch antennas (not visible) are located on the side of the device 10. This enables the device to be applied, but is not limited to the wrist and forearm. The non-invasive testing apparatus 10 has one or more antennas (not visible) on its underside, which make contact, in use, with the skin of the patient. Usefully, this configuration can make use of the relatively high blood flows present under the skin in the wrist region (radial pulse region), as well as the presence of hard bone structures (ulna and radius) located close to the skin surface.

In embodiments of the invention, the antennae 20, 22, 24 function both in transmission and reflection mode. In this manner both the S21 (transmission) and S11 (reflected) signals are measured. The correlation between the blood glucose level and the S11 parameter is derived, together with the S21 parameters such as the resonance frequency shift, "Q" factor of the resonance, group delay, phase, and amplitude variation. In this manner when both the S21 & S11 data are used together, a more accurate value of the blood glucose level is calculated.

Figure 7:
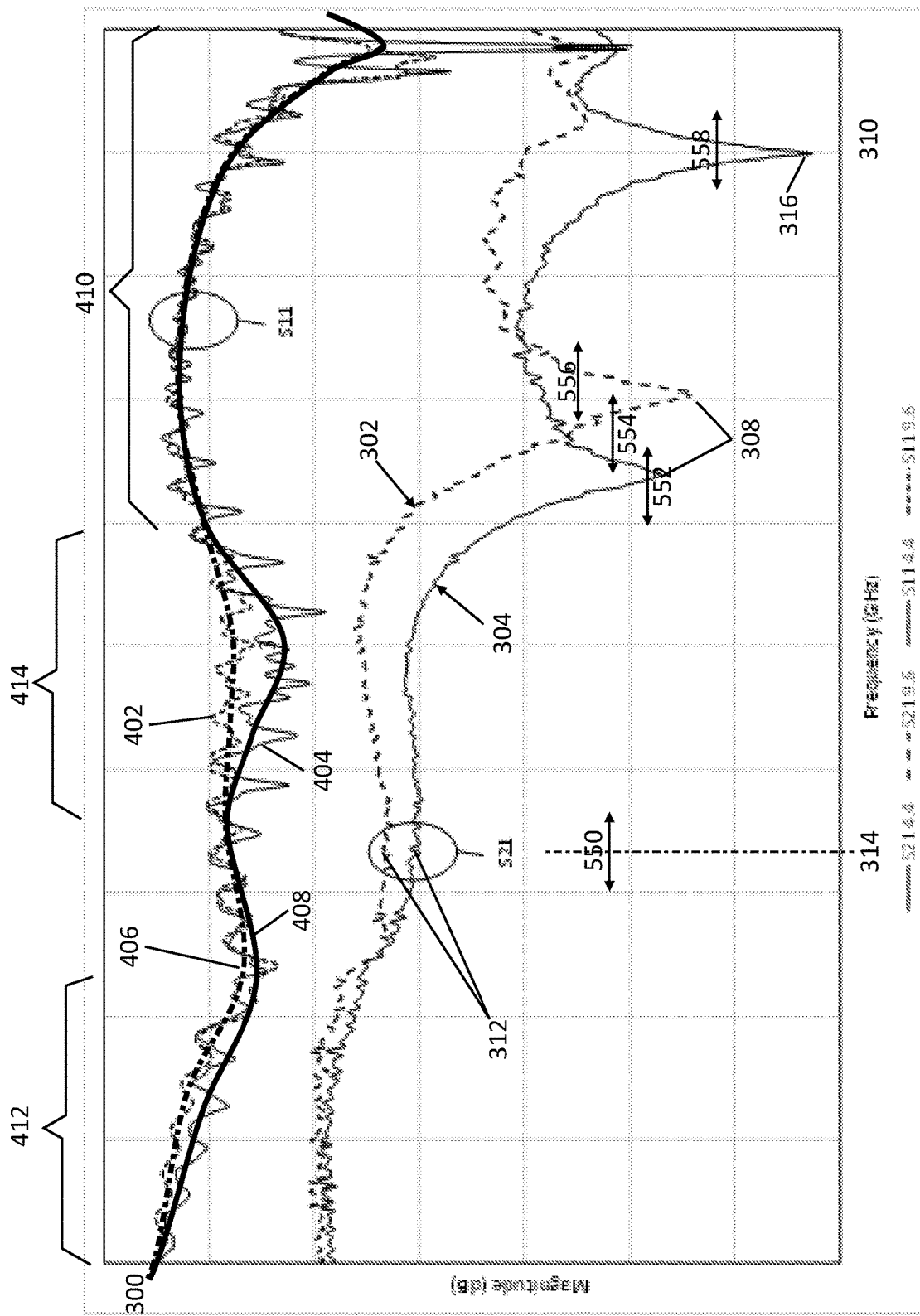
FIG. 7 is graph of amplitude versus frequency for transmitted and reflected signals obtained in accordance with the invention.

FIG. 7 of the drawings is a normalized plot of the magnitude 300 of the received transmitted 302, 304 and received 402, 404 signals as a function of frequency 310 at different blood glucose levels. As can be seen by observing the transmitted signals 302, 304 in the S21 domain, there are characteristic troughs 308 whose positions move as a function of blood sugar concentration. The processor is thus adapted to monitor the points of inflection, i.e. their magnitude and frequency, and to compare these measured values with those in a prepopulated lookup table, from which the blood sugar concertation can be derived. Further, it will be noted that the magnitude 312 of the S21 plot, at certain frequencies 314, changes dependent on the blood sugar concentration, and the processor can be configured to look-up the magnitude 312 at these target frequencies 314 in a pre-populated lookup table to determine the blood sugar concentration.

It will also be seen from FIG. 7, that in the S21 domain, certain characteristic troughs 316 appear at certain blood sugar concentrations. Again, by observing the appearance of these troughs 316, the blood sugar concentration can be observed by reference to lookup tables.

More detailed analysis of the S21 plot 302, 304 can reveal finer textured information, such as from the shape and width of the troughs 308, 316, as well as their frequency and amplitudes. More detailed analysis can be used to verify that the observed effects are consistent with a target substance in the blood (e.g. blood sugar) as opposed to other contamination (e.g. blood alcohol), in which the shape of the observed troughs 308, 316 might be different.

In the S11 domain (the reflected signal), the analysis is more subtle, and requires the processor to analyse the overall shape 406, 408 of the plots 402, 404. It will be apparent from FIG. 7 that in the S11 domain, there are parts 410 of the magnitude 300—frequency 310 plot that are largely independent of the concentration of the target substance (e.g. blood sugar), whereas other parts 412, 414 are dependent on the concentration of the target substance (e.g. blood sugar). Again, these variations as a function of concentration of target substance can be used to obtain the concentration of a target substance (e.g. blood sugar) using, for example, calculations or look-up tables.

Figure 8A:
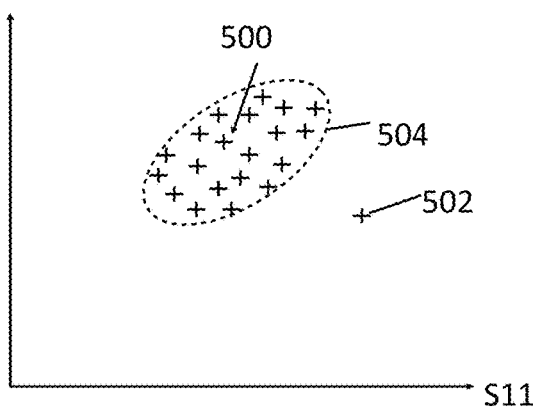
FIG. 8A is a correlation scattergram of the transmitted and reflected signal data of FIG. 7.

One advantage of using both transmitted signal 302, 304 analysis and reflected signal 402, 404 analysis, is the ability to cross check the results to obtain higher accuracy readings, or to provide a failsafe against incorrectly interpreting the presence of contaminants. FIG. 8A, for example, is a schematic scatter graph showing the correlation between the S21 and S11 data 500, and if a test result 502 falls outside statistically acceptable boundaries 504, then the confidence of the test result can be questioned, for example, indicating that a re-test is required, or alerting the patient to the possibility of other contamination.

Figure 8B:
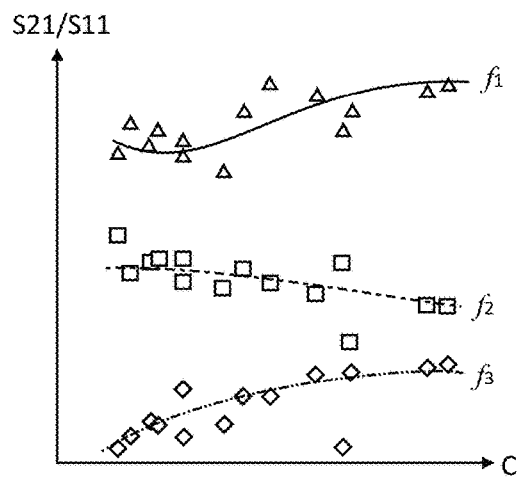
FIG. 8B is a schematic graph showing a correlation between S21/S11 measurements and blood glucose concentration.

Nevertheless, as can be seen from FIG. 8B of the drawings, which is a plot on the vertical axis of S21 or S11 measurement versus blood glucose concentration on the horizontal axis at three different frequencies (f1, f2, f3), that there is a correlation between measured S21 or S11 values and the blood glucose concentration. FIG. 8B, which is schematic, also includes trendlines, which correspond to "polynomial models", or equations, for blood glucose concentration at each of the frequencies. It can be seen that statistical outliers are easily identified from this and can be disregarded from certain test results.

Figure 9:
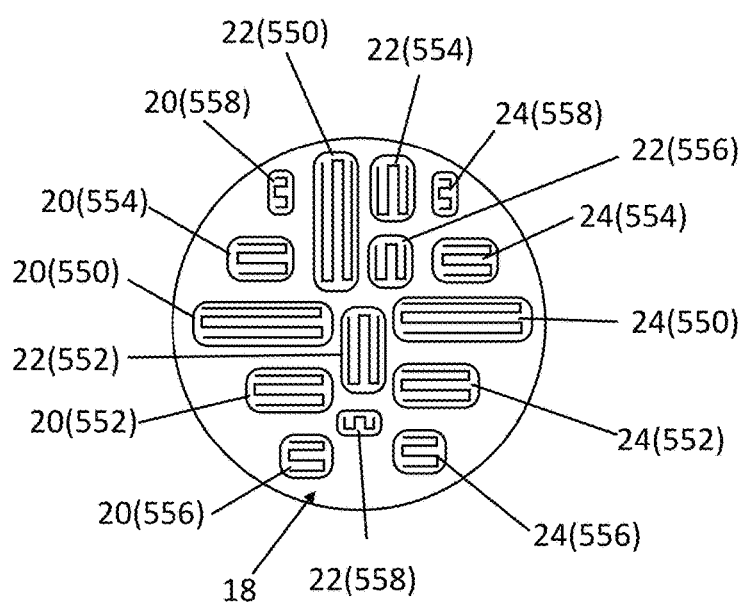
FIG. 9 is a schematic view of a set of frequency-matched antennas for a non-invasive testing apparatus in accordance with the invention.

FIG. 9 of the drawings shows how the frequency specificity shown in FIG. 7 of the drawings can be capitalized upon by using a number of relatively narrow-band antennas, for example, each being tuned to specific narrow frequency bands 550, 552, 554, 556, 558 in which target observations are required. The use of a set of relatively narrow-band antennas enables observations to be made at numerous frequencies simultaneously, thus reducing the time taken for a scan/spectroscopic analysis; as well as increasing the sensitivity of the antennas in their frequency bands, rather than employing a less-sensitive broadband antenna.

The frequency sweep, transmitter & detector circuits may be generated as defined in Patent U.S. Pat. No. 8,882,670 and its derivatives/family.

In another embodiment, an impulse signal may be generated into the biological tissue and the Fast Fourier Transform performed on the received/detected signal in order to derive the frequency response of the system.

Figure 10:
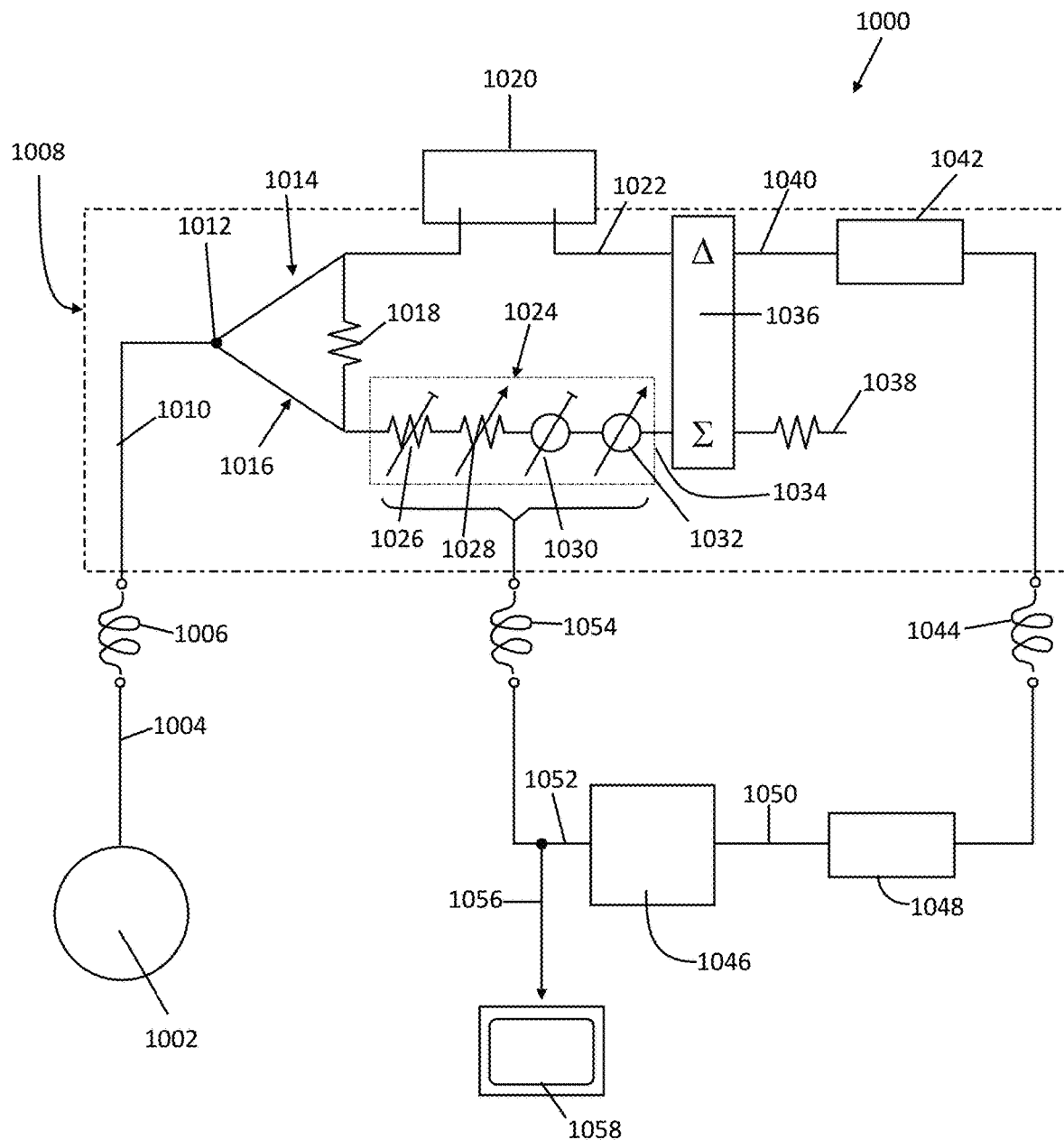
FIG. 10 is a schematic diagram for a first circuit embodying the invention.

Referring to FIG. 10 of the drawings, a circuit 1000 comprises an RF signal generator 1002 adapted, in use, to provide an RF signal at its output 1004. The RF signal generator 1002 is connected, via a fly lead 1006 to a test device 1008 in accordance with an aspect of the invention. The fly lead 1006 connects to an input 1010 of the test device 1008, which connects to an input node 1012 that splits the RF signal equally into a test component 1014 and a reference component 1016. A resistor, 1018 is used to balance the test 1014 and the reference 1016 components.

The test component 1014 is transmitted into a sample 1020 for analysis. Transmission of the test component 1014 into the sample 1020 is typically accomplished by way of a transmit and/or receive antenna (not shown), which couples the test component 1014 of the RF signal to the sample 1020 and receives a response signal 1022.

Meanwhile, the reference component 1016 of the RF signal passes through an adjustable reference circuit 1024, which comprises one or more variable attenuators 1026, 1028, and one or more variable phase shifters 1030, 1032.

The output 1034 of the adjustable reference circuit 1024, along with the output 1022 of the test component 1014 of the RF signal are provided as inputs to a comparator 1036. Typically, the comparator 1036 comprises an analogue bridge-type circuit, such as a Wheatstone bridge-type device, which has a summing output 1038, which is not relevant to this disclosure, and a difference output 1040, which is relevant to this disclosure. The difference output 1040 is the difference between the output 1022 of the test component 1014 of the RF signal and the output 1034 of the adjustable reference circuit 1024.

If the output 1022 of the test component 1014 of the RF signal is equal to the output 1034 of the adjustable reference circuit 1024, then the difference 1040 at the output of the comparator 1036 will be zero. Thus, if the adjustable reference circuit 1024 can be adjusted such that its amplitude and phase match the specimen under test 1020, then the adjustable reference circuit 1024 will essentially be an analogue of the test specimen 1020 and the difference output 1040 of the comparator 1036 will be zero. The key to the invention, therefore, is adjusting the adjustable reference circuit 1024 to meet these criteria.

In order to achieve this, an RF demodulator 1042 is provided downstream of the difference output 1040 and that is connected, via a fly lead 1044 to a microprocessor 1046. An amplifier/demodulator/signal processing device 1048 may be interposed between the difference output 1040 and the microprocessor 1046, and the details of this 1048 are beyond the scope of this disclosure as they will be readily-understood by the skilled reader. Nevertheless, it will be appreciated, that the difference 1040 of the comparator 1036 provides an input 1050 for the microprocessor 1046, which is suitably a DC signal that is proportional to the difference 1040 at the output of the comparator 1036; and/or a PWM signal that is representative of the difference 1040 at the output of the comparator 1036.

The microprocessor 1046 has an output 1052, which is typically connected, via a fly lead 1054, to the adjustable reference circuit 1024. The output 1052 of the microprocessor 1046 contains signals which can be used to adjust the parameters of the variable attenuators 1026, 1028 and the phase shifters 1030, 1032.

The microprocessor effectively executes an algorithm, which adjusts the variable attenuators 1026, 1028 and the phase shifters 1030, 1032 incrementally or continuously until the zero-output condition 1040 at the output of the comparator 1036 is met.

There are various ways that his may be achieved in practice and they will be readily apparent to a person skilled in the art. Nevertheless, and for the purposes of clarification only, in one possible embodiment of the invention, the variable attenuators 1026, 1028 are adjusted (up/down) until the output 1040 of the comparator is minimised (i.e. reaches a minima); then, the phase shifters 1030, 1032 can likewise be adjusted (up/down) until the output 1040 of the comparator 1036 is minimised yet again. This process can be repeated over and over until such time as the output 1040 of the comparator 1036 reaches a minimum, which is ideally a zero output. If/when a zero output, or a substantially zero output 1040, of the comparator is obtained, then the amplitude and phase of the adjustable reference circuit 1024 are essentially an analogue of the test specimen 1020. Thus, the adjustment settings of the adjustable reference circuit are equivalent to the amplitude and phase, and hence, are representative, of the parameters of the test specimen 1020. These parameters can be outputted 1056 to a display 1058 and therefore it is possible to ascertain the amplitude and phase equivalence of the specimen under test.

Ideally, these parameters are not presented to a user in a "raw" state, but are processed in such a way as to provide an indication of the concentration of a target substance, which is ultimately the information that the end-user wants/needs. This can be presented graphically and/or numerically and/or audibly (the latter being beneficial for non-sighted patients and/or where the display may not be easily visible).

It will be appreciated that due to the input node, the test component 1014 and reference component 1016 of the RF signal are equal and because they are compared immediately after the specimen test 1022 and immediately after the adjustable reference circuit 1024, they are effectively independent of the remaining conditions of the circuit, namely the fly leads, etc.

It will also be appreciated that in practical embodiments of the invention, the three fly leads 1006, 1054, 1044 could/would be combined into a single fly lead, but this is not essential.

Nevertheless, it will be appreciated that the invention as described herein, greatly simplifies an RF measurement because it avoids the need for complex signal generating and signal processing devices, such as network analysers. It is also independent of the physical configuration of the set-up and is thus more immune to extraneous variations in its test results.

In certain embodiments of the invention, the RF signal generator 1002 comprises a signal generator that is adapted to output an RF signal 1004 at its output, which has a specific frequency, phase, and amplitude. This could, in certain embodiments, be achieved by using a quartz crystal resonator tuned to a particular frequency, although other RF signal generation technologies are within scope of this disclosure. Nevertheless, it will be appreciated that the parameters of the adjustable reference circuit 1024 can be adjusted, by the microprocessor 1046, to obtain an analogue of the sample under test 1020 for a particular RF signal outputted 1004 from the RF signal generator. Once a test result has been obtained, and optionally outputted 1058, the RF signal generator 1002 can be adjusted to provide a different RF signal, for example having a different frequency, amplitude and/or phase. The test procedure can be repeated for this new RF signal and a further set of parameters obtained.

The RF signal generator 1002 can be configured to "sweep" a particular frequency range, that is to say to vary the frequency of the output continuously, in which case the microprocessor 1046 must be capable of "following" that sweep and determining the parameters of the adjustable reference circuit 1024 almost in real-time. Alternatively, the RF signal generator 1002 may be configured to step through a series of discreet frequencies and the microprocessor 1046 can thus be configured to obtain the parameters of the adjustable reference circuit 1024 for each increment of the output signal 1004 of the RF signal generator 1002. In either case, it is possible to obtain a "spectral" analysis of the sample under test 1020 and thus yield the RF properties of the sample under test 1020.

Figure 11:
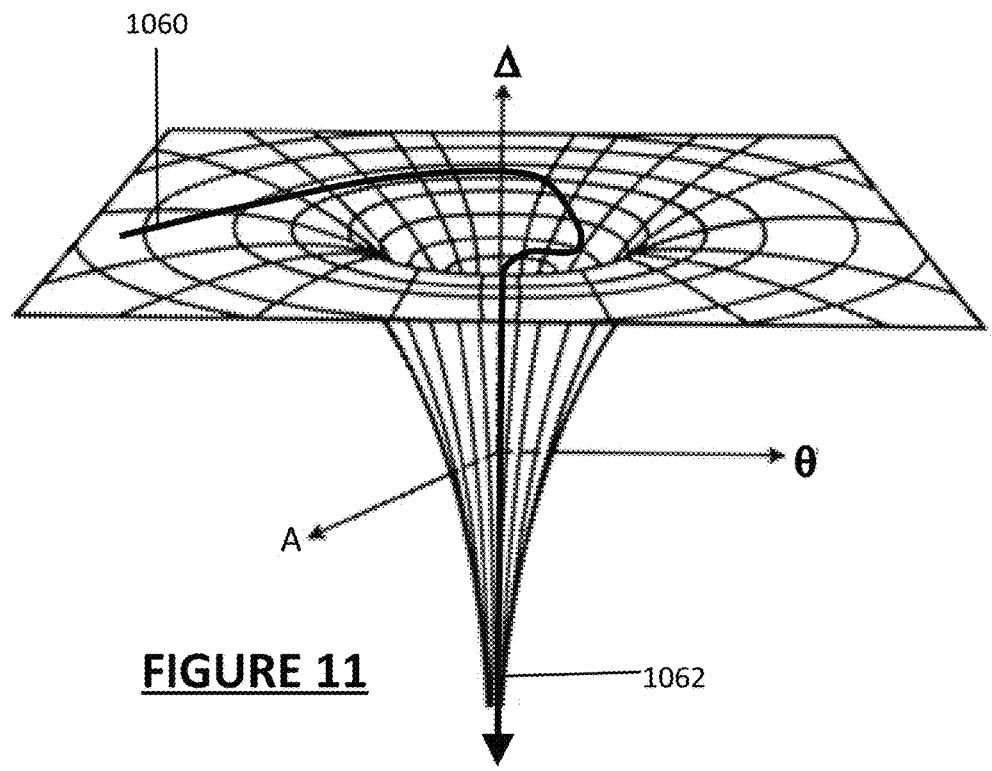
FIG. 11 is a schematic diagram illustrating how the attenuator and phase-shifter settings for the circuit of FIG. 10 can be obtained.

Referring now to FIG. 11 of the drawings, a method by which the microprocessor 1046 obtains the parameters of the variable attenuators 1026, 1028 and the variable phase shifters 1030, 1032 to achieve the zero-difference output 1040 is shown. In FIG. 11, the difference (Δ) at the output 1040 is plotted on the vertical axis, and the attenuation (A) and phase (θ) plotted on the horizontal axes. The microprocessor 1046 varies the parameters of the variable attenuators 1026, 1028 and the variable phase shifters 1030, 1032, as indicated by the path 1060 until the difference (Δ) reaches zero 1062, or is minimised as much as possible. Obviously, any real surface plot of difference (Δ) versus amplitude (A) and phase (θ) will not be as shown in FIG. 11, but FIG. 11 merely indicates how the microprocessor can "seek" the minimum 1062 by varying together, or sequentially, the settings of the variable attenuators 1026, 1028 and the variable phase shifters 1030, 1032 of the reference circuit 1024.

Turning now to FIGS. 12 and 13 of the drawings, a known wearable device 2000 comprises a main body 2002, which has a strap 2004 that passes around a wearer's wrist 2006. The main body 2002 has a transmit/receive antenna 2008 on its underside, in contact with the skin of a patient. The transmit/receive antenna 2008 transmits an RF signal 2010, which is detected by a receive antenna 2012 formed in a housing 2014 located on the opposite side of a user's wrist. The attenuation and/or phase of the transmitted signal 2010 is detected by the device 2000 and a reading is thus obtained.

Additionally or alternatively, the housing 2014 comprises an RF reflector that reflects a transmitted signal 2016 back towards the transmit/receive antenna 2008 of the main body 2002. Again, differences in the attenuation and/or phase of the reflected signal 2018 are picked up by the transmit/receive antenna 2008 of the wearable device 2000 and a reading can thus be obtained.

It will be appreciated from the schematic illustration of FIG. 12, that the known wearable device 2000 requires the housing 2014 to be at a fixed position relative to the main body 2002 such that the transmitted signal 2010 can be picked-up by a receiver 2012 of the housing 2014; or so that the transmitted signal 2016 can be reflected off the reflector of the housing 2014 back to the transmit/receive antenna 2008 of the main body 2002. To achieve this, some form of predetermined alignment 2020 is required between the main body 2002 and the housing 2014.

However, referring to FIG. 13 of the drawings, if the strap 2004 is adjusted, for example to accommodate a different-sized wrist 2006', then the alignment of the main body 2002 relative to the housing 2014 is now broken. This can result in the transmitted signal 2010 "missing" the receiver 2012 incorporated into the housing 2014; or failure of the reflector of the housing 2014 to reflect back the transmitted signal 2016 in the manner previously described.

It will be appreciated, therefore, that adjustment of the wrist strap 2004 to fit different user's wrist sizes can result in the known wearable device 2000 becoming ineffective.

Turning now to FIGS. 14 and 15 of the drawings, a wearable device 3000 in accordance with the invention is described. In this case, the wearable device 3000 comprises a main body 3002, which comprises a transmit/receive antenna 3004, which sends a transmit signal 3006 to a receiver 3008 incorporated into a housing 3010 placed opposite the main body 3002.

Additionally or alternatively, the transmit/receive antenna 3004 can send out a signal 3012 which is reflected off a reflector incorporated into the housing 3010 to reflect the signal 3014 back to the transmit/receive antenna 3004 of the main body. It can be seen that the main body 3002 and housing 3010 are aligned and lie on a centreline 3016, which, ideally, passes through the centres of the main body 3002 and housing 3010 and, preferably still, at right angles to both.

The wearable device 3000 comprises a strap 3020, which has a fixed end 3022, which passes around the left-hand side (in the drawing) of the user's wrist 2016, around a pully/roller 3024 connected to the left-hand side (in the drawings) of the housing 3010 and back around the user's wrist 2016. The strap 3020 passes underneath (in the illustrated embodiment, although it could be over) the main body 3002, around a further set of optional guide rollers 3026 and then around the right-hand side (in the illustrated embodiment) of the user's wrist 2016 to a further roller 3028. The strap 3020 then passes back around the right-hand side of the user's wrist (in the illustrated embodiment) and terminates in a free end 3030, which can be secured 3032 back on Suitably, the at least one antenna is operatively coupled to the skin of a patient, and hence to the patient's blood.

It will be appreciated that the strap 3020 has two strap portions 3024, 3026 of approximately equal lengths on either side of the user's wrist 2016. This "pulley type" configuration means that when the free end 3030 of the strap 3020 is pulled, the strap will shorten equally on either side of the user's wrist 2016 resulting in the housing 3010 being drawn towards the main body 3002 in a substantially straight line—thereby maintaining the desired alignment between the main body 3002 and the housing 3010.

Turning to FIG. 15 of the drawings, it can be seen that the same wearable device 3000 has been fitted to a different sized user's wrist 2016' and that the alignment of the main body 3002 relative to the housing 3010 has been preserved. It will be appreciated by comparing the invention of FIG. 15 with the prior art as illustrated in FIG. 13, that in this case, adjustment of the strap 3020 does not result in breaking the requisite alignment of the housing 3010 relative to the main body 3002 and therefore, the transmitted 3006 and reflected 3012 3014 signals do not "miss" their respective targets, namely the receiver/reflector of the housing 3010 located on the opposite side of the wrist 2016 to the main body 3002.

Therefore, a wearable device 3000 in accordance with the invention, can be reliably fitted to different wrist sizes and still maintain its functionality, unlike known wearable devices 2000 (as shown in FIGS. 12 and 13, for example) where adjustment to the strap 2004 can result in misalignment of the housing 2014 relative to the main body 2002, or in other words—unequal spacing on opposite sides of the wrist between the main body 2002 and the housing 2012.

Turning now to FIGS. 16 and 17 of the drawings, another embodiment of a wearable device 4000 in accordance with certain aspects of the invention is shown, schematically in cross-section. Again, the wearable device 4000 comprises a main body 4002 which is held onto a user's wrist 4004 using an adjustable strap 4006. The strap can be adjusted using a clasp 4008, buckle or other suitable device.

In FIG. 16 it can be seen that the wearable device 4000 is worn loosely around the wrist 4004 and thus there is a small air gap 4010 between the underside of the main body 4002 and the skin surface 4012 directly beneath it. The main body 4002 comprises an RF antenna 4014 which, in order to work correctly, needs to be coupled effectively to the surface 4012 of the user's skin. With the wearable device 4000 fitted loosely, as shown in FIG. 16, this is not possible or reproducible due to the air gap 4010 between the antenna 4014 and the user's skin 4012.

To address this issue, the wearable device 4000 comprises an inflatable air bladder 4016, which is interposed between a rear surface 4018 of the antenna 4014 and the main body 4002. The air bladder 4016 can be inflated using a pump, which in the illustrated embodiment, comprises a small sac 4020 that can be pressed repeatedly to expel air into the bladder 4016 via a small tube 4022.

Referring now to FIG. 17 of the drawings, it can be seen that the sac 4020 has been pressed 4024 repeatedly and air within it has been discharged, via the tube 4022 into the bladder 4016 which has now become inflated. Interposed between the sac 4020 and the airbladder 4016 is a one-way/pressure-relief valve 4026, which ensures, on the one hand, that air expelled from the sac 4020 is directed into the bladder 4016; and which also prevents over-inflation of the airbladder. The setting of the pressure-relief valve 4026 can be adjusted (or factory set) such that the internal air pressure 4028 within the air sac 4016 is sufficient to ensure that the force 4030 applied by the antenna 4014 onto the surface of the user's skin 4012 is at least a predetermined press-on force.

It will be appreciated that because the airbladder 4016 is inflated using air pressure, that the internal pressure 4028 will be hydrostatic, that is to say applied evenly to the rear surface 4018 of the antenna 4014 and thus the press-on force 4030 of the antenna 4014 onto the skin surface 4012 will be substantially even across the entire surface of the antenna 4014 also.

Not shown in the drawings is an electronic air pressure sensor located within the air bladder 4016, which emits an audible and/or visual signal via a display/audible output of the wearable device 4000 when the internal air pressure 4028 was in the airbladder 4016 is below the predetermined pressure. Thus, a user can, when either alerted or wishes to carry out a test, inflate the bladder 4016 using the sac 4020 by pressing 4020 repeatedly upon it. Air from the sac 4020 will be expelled into the bladder 4016 to inflate it and—up to the point that the minimum required pressure has been reached, the audible and/or visual signal will sound/display indicating to the user to carry on pressing the sac 4020. Upon reaching the desired internal pressure 4028, the pressure relief valve 4026 will operate to prevent further air entering, and thus over-inflating, the airbladder. At the same time, the air pressure sensor will trigger the wearable device 4000 to stop emitting a "keep pumping" signal and thus the user can be sure that the air bladder has been correctly inflated, and the required press-on force 4030 has been attained. An RF test, using the antenna 4014 can then be commenced in a manner described herein.

It will be appreciated that the embodiment of the invention shown in FIGS. 16 and 17 enables a wearable device 4000 to be worn loosely/in accordance with user preference for most of the time, but readily enables the antenna 4014 to be pressed onto the user's skin 4012 with a predetermined and easily reproducible force thereby ensuring reproducibility of an RF test carried out using the antenna 4014. At the end of the test, the airbladder 4016 can be deflated, at which point the "comfort setting" of the strap, 4006 returns to its pre-test state and the user can carry on.

Turning now to FIGS. 18 and 19 of the drawings, self-adhesive antenna patch 5000 in accordance within embodiments of the invention is shown, which has on its underside, one or more antennas 20, 22, 24 as described previously with reference to FIGS. 1, 2 and 9, etc. above. The antenna or antennas work in the manner previously described to obtain an RF test result. The underside of the self-adhesive antenna patch 5000 comprises a central region 5002 which is non-, or largely non-adhesive surrounded by a self-adhesive region 5004 that is covered with a water-resistant, pressure-sensitive adhesive—as will be well understood to the skilled reader.

The self-adhesive antenna 5000 can therefore be stuck onto a patient's skin (not shown) and remain there for a period of time. As such, during the time that the self-adhesive antenna patch 5000 is adhered to the patient's skin, any test results obtained using the antenna(s) will be independent of variations in the location of the antennas relevant to the patient's body. This overcomes many of the extrinsic variables associated with taking RF readings on a patient that moves a lot.

The top side of the self-adhesive antenna patch 5000 is shown in FIG. 19 of the drawings, and comprises a button type connector 5006, which provides one or more electrical contacts for a test circuit (not shown) interposed between the connector 5006 and the antennas on the underside of the self-adhesive antenna 5000 is a calibration circuit 5008, which shall be described below.

Referring to FIG. 20 of the drawings, the calibration circuit 5008 is interposed between the connector 5006 and the antenna, indicated schematically as 20 in FIGS. 20, 21 and 22, although it will be appreciated that, in reality, the antennas 20 are more like those shown in FIG. 18 of the drawings. The connector 5006 comprises a signal line 5010 to which is applied a test RF signal 5012 by a signal generator/analyser 5014 connected, via a fly lead 5016 to a complimentary connector 5018 at its free end. The fly lead's connector 5018 electrically connects to the connector 5006 of the self-adhesive antenna 5000 in a manner that will be readily understood. The fly lead 5016 is shielded by a grounding sheath 5020, which is grounded 5022 in the manner that will be readily understood to the skilled reader.

Therefore, a test signal 5010 can be sent to the antenna 20 via the fly lead 5016 and the calibration circuit 5008.

The calibration circuit 5008 comprises a solid-state switch, which is a single pole-four throw switch having four output terminals. A first one of the output terminals 5024 is not connected to anything and thus is an open-circuit connection. A second one of the output terminals 5026 is connected to the antenna 20. A third one of the output terminals 5028 is connected to ground 5022 via a reference load 5030 (typically a 50-ohm load). Finally, a fourth output terminal 5032 is connected directly to ground 5022.

The input pole 5034 of the solid-state switch 5022 can thus be connected to any one of the four output terminals 5024, 5026, 5028, 5032 to carry out an open-circuit calibration routine, a closed-circuit test routine and a reference load test routine. By putting these test results into a suitable matrix, the transmission system, that is to say the fly lead 5016 and connectors 5018, 5016 can be calibrated-out and thus the actual RF signal response of the antenna can be more accurately measured regardless of the instantaneous configuration of the fly lead 5016 and connectors 5018, 5006.

It will be appreciated that being able to cancel-out any errors in the transmission system represents a big step forward in RF measurement because variables associated with the physical setup of the test apparatus can effectively be ruled-out using an in-situ calibration device. Additionally, because the in-situ calibration device 5008 is relatively simple and inexpensive, it is possible to make this a "disposable" part of the self-adhesive patch antenna 5000, which in-turn facilitates mass production of the same.

The on-board/in-situ calibration apparatus previously described can, of course, be used on a transmit-receive system, such as a clamp-on device as shown in FIG. 5 of the drawings. Referring to FIG. 5 of the drawings, the clamp-on probe 156 comprises a transmit antenna 20 on one side of an earlobe 90 and a receive antenna 24 located on the opposite side of the earlobe 90.

The probe 156 is connected via fly lead 154 to a RF signal generator analyser and is thus potentially susceptible to substantial amounts of extrinsic variables. However, by incorporating an on-board calibration device to each of the antennas 20, 24, it is possible to calibrate-out any such extrinsic variables in the manner previously described.

For the sake of completeness, a typical calibration device 5008 suitable for us in conjunction with the probe 156 of FIG. 5 is shown. In essence, the calibration device comprises two calibration devices as shown in FIG. 20, but with the addition of a bypass conductor 5050 which bypasses the transmit 20 and receive antennas 24 and so a signal 5010 can be transmitted from a transmitter 5014 via a fly lead 5016/ connector 5018, 5006, through the bypass conductor 5050 and back to the signal generator/analyser 5014 via the same, or a different fly lead 5016. It will be appreciated, that in this embodiment, the switch means 5022 comprises a fifth throw position 5052, which enables the test signal 5010 to be transmitted via the bypass conductor 5050 directly back to the RF signal generator/analyser 5014 and therefore, calibrate the fly lead 5016 and connectors 5018, 5006 out of the system.

It would also be appreciated that either of the switches 5002 can be set to the previously described positions, namely open-circuit closed-circuit and reference load to calibrate each of the antennas 20, 24 independently as well. It will be appreciated that the invention thus overcomes many of the practical restrictions/problems associated with using RF measurements techniques in situations where the subject and/or test equipment can move considerably.

Finally, referring to FIG. 22 of the drawings, a self-adhesive antenna patch 5000 has been stuck to the patient's skin 4012 on the patient's wrist 4004 in a similar manner to that shown in FIGS. 16 and 17 of the drawings. However, rather than having to tighten the strap 4006, or inflate an air bladder 4016 to obtain the required contact between the antennas and the skin 4012 of the patient's wrist 4004, this is semi-permanently achieved by using a self-adhesive antenna patch. The connector 5006 comprises a button-type connector, which engages a complimentary socket 5060 provided on the underside of a wearable device 4000. Thus, the wearable device 4000 is able to achieve a calibrated connection to the self-adhesive patch antenna 5000 whilst ensuring that the self-adhesive patch antenna always stays in the same place relative to the patient's wrist 4004 from one test to the next.

Embodiments of the invention may allow the measurements taken to be transmitted to external devices to monitor their blood-glucose level whilst using their home computer or smart phone or similar device and allow for remote logging of blood-glucose levels. This feature could prove to be most useful for carefully monitoring the condition of elderly sufferers and enable medical practitioners to provide emergency help should the patient's levels become excessively high or low. Remote monitoring and data logging can also be used to provide a useful tool to the patient or the doctor/healthcare professional to develop a response plan to assist with the management of the disease.

The following statements are not the claims, but relate to various possible features of the invention:

Statement 1. A non-invasive testing apparatus for determining a concentration of a target substance in a patient's blood, the non-invasive testing apparatus comprising: an RF signal generator adapted, in use, to output an output RF signal; a processor; and at least one antenna operatively coupled, in use, to patient's blood, the or at least one antenna being operatively connected to the RF signal generator and the processor, characterised by the processor being adapted, in use, to: measure a response signal via at least one of the antennas, the response signal being a function of the output RF signal modified by an interaction with the patient's blood, measure the amplitude and phase of the response signal at a plurality of output RF signal frequencies; plot the measured amplitude and phase of the response signal as a function of output RF signal frequencies using the plot, determine any one or more derived parameters of the response signal from the group comprising: a resonance frequency shift; a Q factor of the resonance; a group delay; a phase shift; an amplitude variation; a shape factor of the plot; and a gradient of the plot at different frequencies; compare any one or more of the derived parameters with a model of the respective derived parameters as a function of concentration of the target substance in blood; and to determine a concentration of the target substance in the patient's blood based on a correlation between the derived parameter or parameters and the corresponding values of concentration of the target substance in the patient's blood in the model.

Statement 2. The apparatus of statement 1, wherein the processor is adapted to: determine a plurality of derived parameters; compare the plurality of derived parameters with respective models of the respective derived parameters as a function of concentration of the target substance in blood; to determine, for each derived parameter, a concentration of the target substance in the patient's blood based on a correlation between the respective derived parameter and the corresponding values of concentration of the target substance in the patient's blood in the respective model; and to apply a statistical model to the resulting determined concentrations of the target substance in the patient's blood based on each derived parameter to arrive at a single, overall determined concentration of the target substance in the patient's blood.

Statement 3. The apparatus of statement 1 or statement 2, wherein the or each model comprises a lookup table of derived parameters and their corresponding concentrations of the target substance in the patient's blood, and wherein the processor is adapted to identify the closest match to data in the lookup table or to interpolate between data in the lookup table to arrive at a determined concentration of the target substance in the patient's blood.

Statement 4. The apparatus of any preceding statement, wherein the or each model comprises an equation defining a relationship between a derived parameter and concentration of the target substance in the patient's blood, and wherein the processor is adapted to use the derived parameter as the argument of the equation to yield the value being the concentration of the target substance in the patient's blood.

Statement 5. The apparatus of any preceding statement, wherein the response signal comprises a transmitted response signal.

Statement 6. The apparatus of any preceding statement, wherein the response signal comprises a reflected response signal.

Statement 7. A non-invasive testing apparatus for determining a concentration of a target substance in a patient's blood, the non-invasive RF testing apparatus comprising a circuit comprising: an RF signal generator adapted, in use, to provide an RF signal at its output, the output of the RF signal generator being connected, in use, to an input node, the input node being configured, in use, to split the RF signal into sustainably equal first and second signals, the first signal being connected to a test output at least one antenna coupled to a patient's body part containing blood to be analysed for the target substance, the second signal being connected to a reference output via an adjustable reference circuit, the test and reference outputs being connected, in use, to respective inputs of a comparator, the comparator being adapted in use to output, at a comparator output, a difference between the test output and the reference output, the circuit further comprising a microprocessor comprising: a microprocessor input connected, in use, to the comparator output; and a control output connected, in use, to the reference circuit; wherein the reference circuit comprises a variable attenuator and a variable phase shifter controllable, in use, by the control output of the microprocessor, and wherein the microprocessor is adapted, in use, to: adjust its control output and thereby adjust the amplitude and phase of the reference circuit so as to bring the comparator output to zero, or substantially zero, whereby the adjustable reference circuit is adjusted such that it is an analogue of the to a patient's body part containing blood to be analysed for the target substance; and to output a data signal indicating the amplitude and phase of the reference circuit where the comparator output is zero, or substantially zero.

Statement 8. The apparatus of any of statements 1 to 6, comprising the circuit of statement 7, wherein the measured amplitude and phase of the response signal are derived from the data signal indicating the amplitude and phase of the reference circuit where the comparator output is zero, or substantially zero.

Statement 9. The apparatus of statement 7 or statement 8, wherein the effective path lengths of conductors carrying the first and second signals between the input node and the inputs of a comparator are equal or substantially equal.

Statement 10. The apparatus of statement 7, 8 or 9, wherein the comparator comprises a bridge-type circuit.

Statement 11. The apparatus of any of statements 7 to 10, further comprising means for converting the comparator output into a DC or PWM signal at the microprocessor input, the DC or PWM signal being proportional to the comparator output.

Statement 12. The apparatus of any of statements 7 to 11, wherein the data signal indicating the amplitude and phase of the reference circuit where the comparator output is zero, or substantially zero is represented on a display device, such as a display screen, an LCD panel, or one or more dials.

Statement 13. The apparatus of any preceding statement comprising a fly lead connecting any one or more of: the RF signal generator and the input node; the comparator output and the microprocessor input; the microprocessor's control output and the reference circuit; the RF signal generator and an antenna; and an antenna and the processor.

Statement 14. The apparatus of statement 13, wherein the or each fly lead comprise a detachable connector.

Statement 15. A calibration apparatus comprising: an antenna connected to a connector having a connector input connectable, in use, to a corresponding connector of a fly lead or other device; and switch means interposed between an output of the connector and the antenna, the switch means having an input connected to output of the connector, a first output connected to the antenna, a second output connected to an open circuit, a third output connected to ground, and a fourth output connected to a reference load, wherein the switch means is actuatable, in use, to selectively connect the connector to each of the four outputs individually such that, in use, the antenna can be calibrated relative to a signal transmission system connected to the input of the connector.

Statement 16. The apparatus of any of statements 1 to 14 comprising the calibration apparatus of statement 15.

Statement 17. The apparatus of statement 15 or statement 16, wherein the switch means comprises a solid-state switch.

Statement 18. The apparatus of statement 15, 16 or 17, wherein the reference load comprises a substantially 50Ω load.

Statement 19. The apparatus of any of statements 15 to 18, wherein the switch means is adapted to cycle an input RF signal to each of its four outputs in sequence, such that measured responses for each switch position can be analysed and used in a calibration algorithm or matrix to calibrate the antenna and thereby factor-out variables associated with a connected signal transmission system.

Statement 20. The apparatus of any of statements 15 to 19, wherein the switch means further comprise a fifth output position, which connects the output of a first connector associated with a first antenna to an output of a second connector associated with a second antenna.

Statement 21. The apparatus of any preceding statement, wherein the RF signal generator is adapted to output signals in the range of 8 GHz to 30 GHz.

Statement 22. The apparatus of any preceding statement, wherein the RF signal generator comprises a stable resonator circuit capable of outputting an RF signal having a substantially constant amplitude, frequency, and phase.

Statement 23. The apparatus of any preceding statement, wherein the RF signal generator comprises means for selectively adjusting any one or more of the amplitude, frequency, and phase of the RF signal at its output.

Statement 24. The apparatus of any preceding statement, wherein the RF signal generator is adapted to continuously adjust any one or more of the frequency, amplitude, and phase of the RF signal at its output.

Statement 25. The apparatus of statements 1 to 23, wherein the RF signal generator is adapted to incrementally adjust any one or more of the frequency, amplitude, and phase of the RF signal at its output.

Statement 26. The apparatus of statement 25, wherein the RF signal generator comprises a plurality of resonators, each being configured to output a different frequency, amplitude and/or phase RF signal, and switch means for selectively connecting a selected one of the plurality of the resonators to the RF signal generator's output such that the RF signal generator can selectively output an RF signal having a selected frequency, amplitude and/or phase.

Statement 27. The apparatus of statement 26, comprising a plurality of frequency-matched antennas, each frequency-matched antenna being tuned to a particular bandwidth and wherein the RF signal generator is configured to output a corresponding plurality of narrow-bandwidth output signals to each of the frequency-matched antennas.

Statement 28. The apparatus of any preceding statement, wherein the RF signal generator is configured to output a 1 to 10 ms burst signal, and wherein the processor is adapted to transpose the response signal from the time domain into the frequency domain to obtain a frequency spectrum from the burst signal.

Statement 29. The apparatus of statement 28, wherein the processor is adapted to apply a Z-transform to derive from the response signal, a frequency spectrum.

Statement 30. The apparatus of any preceding statement, wherein the processor measures the amplitude and phase of the response signals at a plurality of frequencies, and determines the amplitude and frequency of inflection points corresponding to resonance troughs.

Statement 31. The apparatus of any preceding statement, wherein the processor is adapted, in respect of a reflected response signal, to analyse the overall shape of the amplitude-frequency relationship; derive a shape factor for the overall shape in regions where the amplitude-frequency relationship varies as a function of the concentration of the target substance, and determine a concentration of the target substance from the observed shape factor in those regions.

Statement 32. The apparatus of any preceding statement, wherein the processor is adapted to verifying the accuracy of the derived concentration of target substance by plotting the reflected response signal against the transmitted response signal, and by checking that the data point for the derived target substance concentration falls within a statistically acceptable region of a calibrated target substance concentration scattergram.

Statement 33. The apparatus of any preceding statement, comprising an antenna via which the output signal is sent, and via which the transmitted and reflected response signals are received.

Statement 34. The apparatus of any preceding statement, comprising a first antenna via which the output signal is sent, and a second antenna via which the transmitted and reflected response signals are received.

Statement 35. The apparatus of statement 34, wherein the first and second antennas are placed side-by-side on one side of a target body part.

Statement 36. The apparatus of statement 35, wherein the first and second antennas are directional antennas such that, in use, the output signal is directed towards the second antenna, and such that the gain of the second antenna is biased towards the direction of the first antenna.

Statement 37. The apparatus of any preceding statement, wherein the or each antenna comprises a patch antenna.

Statement 38. The apparatus of any preceding statement, further comprising a coupling medium interposed, in use, between the or each antenna and the patient's skin.

Statement 39. The apparatus of statement 37 or statement 38, wherein the or each patch antenna is disposed on the underside of a self-adhesive substrate, and wherein a connector connected to the or each antenna is disposed on an upper surface of the self-adhesive substrate.

Statement 40. The apparatus of statement 39, wherein the RF signal generator and processor are incorporated into the main body of a wrist-watch type device in which the or each complementary connector is provided on its underside, and wherein the wrist-watch type device further comprises a display for displaying the determined concentration of target substance in the patient's blood.

Statement 41. The apparatus of statement 37 or statement 38, wherein the patch antenna is provided on an underside of a wrist-watch type device comprising the RF signal generator and processor and a display for displaying the determined concentration of target substance in the patient's blood, the patch antenna of the wrist-watch type device being held in contact with a patient's skin by a strap of the wrist-watch type device.

Statement 42. A non-invasive testing apparatus for determining a concentration of a target substance in a patient's blood comprising a main body comprising: at least one antenna operatively coupled, in use, to the skin of a patient; and a housing comprising at least one receiver antenna and/or reflector also operatively coupled, in use, to the skin of a patient, the housing being located, in use, on an opposite side of the patient's anatomy to the main body; an adjustable strap connecting the main body to the housing, wherein the strap is formed as a pulley belt affixed at one end to the main body or housing, which is wound around respective rollers of the main body and the housing, and which has a free end, wherein the pulley belt and rollers are configured to centralise the housing relative to the main body such that pulling on the free end of the strap reduces the distance between the main body and the housing, whilst maintaining a substantially constant alignment between the main body and the housing.

Statement 43. A non-invasive testing apparatus of statement 41 comprising the centraliser of statement 42.

Statement 44. The apparatus of statement 42 or statement 43, wherein the rollers that are rotatably affixed to the main body and housing.

Statement 45. The apparatus of statement 42, 43 or statement 44, wherein the strap is anchored at one end to the main body, and passes around a user's wrist or other body part to a first roller located to one side of the housing, wherein the strap folds back on itself and passes around the same side of the user's wrist or body part back towards the main body, wherein the strap extends around to the opposite side of the user's wrist or body part to a second roller located on an opposite side of the housing, such that an equal number of strap lengths are provided on either side of the user's wrist or body part, such that pulling on the free end of the strap causes movement of the housing relative to the main body whereby the strap lengths on either side of the user's wrist or body part are substantially equal, or equal.

Statement 46. A non-invasive testing apparatus for determining a concentration of a target substance in a patient's blood comprising a main body comprising at least one antenna having a front surface operatively coupled, in use, to the skin of a patient and an adjustable strap connected to the main body and extending, in use, around a part of the patient's body to retain the antenna adjacent the patient's skin, the non-invasive testing device further comprising: an air bladder, and means for inflating the air bladder to cause the front surface of the antenna to press against the patient's skin with a predetermined force.

Statement 47. The non-invasive testing apparatus of statement 41, comprising the centraliser or air bladder system of any of statements 42 to 46.

Statement 48. The apparatus of statement 46 or statement 47, wherein the means for inflating the bladder comprises a pump.

Statement 49. The apparatus of statement 48, wherein the pump comprises a manual pump.

Statement 50. The apparatus of statement 49, wherein the manual pump comprises a compressible bladder with an outlet connected, via a one-way valve to an inlet of the air bladder.

Statement 51. The apparatus of any of statements 46 to 50, wherein the means for causing the front surface of the antenna to press against the patient's skin with a predetermined force comprises a pressure-relief valve interposed between the pump and the air bladder.

Statement 52. The apparatus of any of statements 46 to 51, further comprising an air pressure sensor adapted, in use, to indicate, when the air pressure within the air bladder is below an air pressure corresponding to the predetermined force.

Statement 53. The apparatus of any of statements 46 to 52, wherein the air bladder is interposed between the main body and a rear surface of the antenna.

Statement 54. The apparatus of statement 34, further comprising a clamping device comprising first and second clamp parts adapted, in use, to engage opposite sides of a body part; the first and second antennas being incorporated into the clamp parts such that, in use, the signal passes through the body part between the first and second antennas.

Statement 55. The apparatus any preceding statement, wherein the clamping device is located at the end of a fly lead.

Statement 56. The apparatus of statement 55, wherein the clamping device comprises the calibration apparatus of any of statements 10 to 15.

Statement 57. The apparatus of any preceding statement, wherein the processor is integrated into a main body portion of the non-invasive testing apparatus.

Statement 58. The apparatus of any of statements 1 to 56, wherein the processor is physically or logically separate from a main body of the non-invasive testing apparatus.

Statement 59. The apparatus of statement 58, comprising an I/O interface operatively connecting, in use, the driver and processor to a supplementary processing unit.

Statement 60. The apparatus of statement 59, wherein the supplementary processing unit is located in any one or more of the group comprising: a dedicated external processing unit; a smartphone device; a tablet computer device; a personal computer; and on a cloud-based computer server.

Statement 61. The apparatus of any preceding statement, further comprising a human interface device, the human interface device comprising any one or more of the group comprising: a start/stop button; an LED; a beeper; a display screen.

Statement 62. The apparatus of any preceding statement, further comprising a memory for storing either or both of previous test results and lookup tables.

Statement 63. The apparatus of any of statements 1 to 38, comprising a main body portion formed of a first generally cylindrical part and a second generally cylindrical part nested, and slidingly receivable within the first part, switch means interposed between the first and second parts of the main body portion actuable upon relative movement of the first and second parts, and wherein the second part comprises a generally planar end surface upon which are disposed three patch antennas.

Statement 64. The apparatus of statement 63, further comprising an end cap adapted to fit over the second part, the end cap comprising an insert formed from a standard material having known properties, the insert being arranged to engage the patch antennas when placed over the second part.

Statement 65. The apparatus of statement 64, wherein the end cap comprises an electrically conductive rim portion that forms an electrical connection, when placed onto the second part with the insert in contact with the antennas, between a pair of electrodes located on an abutment edge of the first part of the main body.

The invention is not restricted to the details of the foregoing embodiments, which are merely exemplary of the invention.

The invention claimed is:

1. A non-invasive testing apparatus for determining a concentration of a target substance in a patient's blood, the non-invasive testing apparatus comprising:
    an RF signal generator adapted, in use, to output an output RF signal;
    a processor; and
    at least one antenna operatively coupled, in use, to a body part containing the patient's blood, the at least one antenna being operatively connected to the RF signal generator and the processor,
    characterised by the processor being adapted, in use, to:
        measure a transmitted or reflected response signal via at least one of the antennas, the response signal being a function of the output RF signal modified by an interaction with the patient's blood;
        measure the amplitude and phase of the response signal at a plurality of output RF signal frequencies;
        plot the measured amplitude and phase of the response signal as a function of output RF signal frequencies;
        using the plot, determine any two or more derived parameters of the response signal from the group consisting of: a Q factor of the resonance; a group delay; a shape factor of the plot; and a gradient of the plot at different frequencies; and to
        determine the concentration of the target substance in the patient's blood by:
        the processor being adapted to:
        compare the plurality of derived parameters with respective models of the respective derived parameters as a function of concentration of the target substance in blood;
        to determine, for each derived parameter, a concentration of the target substance in the patient's blood based on a correlation between the respective derived parameter and the corresponding values of concentration of the target substance in the patient's blood in the respective model; and
        to apply a statistical model to the resulting determined concentrations of the target substance in the patient's blood based on each derived parameter to arrive at a single, overall determined concentration of the target substance in the patient's blood.

2. The apparatus of claim 1, wherein the processor being further adapted to, using the plot, determine any one or more parameters of the response signal from the group consisting of: a resonance frequency shift; a phase shift; and an amplitude variation.

3. The apparatus of claim 1, wherein each model comprises any one or more of:
    a lookup table of derived parameters and their corresponding concentrations of the target substance in the patient's blood, and wherein the processor is adapted to identify the closest match to data in the lookup table or to interpolate between data in the lookup table to arrive at a determined concentration of the target substance in the patient's blood; and
    an equation defining a relationship between a derived parameter and concentration of the target substance in the patient's blood, and wherein the processor is adapted to use the derived parameter as the argument of the equation to yield the value being the concentration of the target substance in the patient's blood.

4. The apparatus of claim 1, wherein the amplitude and phase of the response signal are measured by a circuit in which:
    the output of the RF signal generator is connected to an input node, the input node being configured, in use, to split the RF signal into substantially equal first and second signals, the first signal being connected to a test output via the antenna,
    the second signal being connected to a reference output via an adjustable reference circuit, the test and reference outputs being connected to respective inputs of a comparator, the comparator being adapted to output, at a comparator output, a difference between the test output and the reference output,
    the circuit further comprising a microprocessor comprising:
        a microprocessor input connected to the comparator output; and a control output connected to the reference circuit; wherein the reference circuit comprises a variable attenuator and a variable phase shifter controllable by the control output of the microprocessor, and wherein the microprocessor is adapted to:

adjust its control output and thereby adjust the amplitude and phase of the reference circuit so as to bring the comparator output to zero, or substantially zero, whereby the adjustable reference circuit is adjusted such that it is an analogue of the body part containing the blood; and to output a data signal indicating the amplitude and phase of the reference circuit where the comparator output is zero, or substantially zero.

5. The apparatus of claim 4, wherein the effective path lengths of conductors carrying the first and second signals between the input node and the inputs of the comparator are equal or substantially equal.

6. The apparatus of claim 4, further comprising any one or more of:

means for converting the comparator output into a DC or PWM signal at the microprocessor input, the DC or PWM signal being proportional to the comparator output; and a display device, wherein the data signal indicating the amplitude and phase of the reference circuit where the comparator output is zero, or substantially zero is represented on the display device, being a display screen, an LCD panel, or one or more dials.

7. The apparatus of claim 4, comprising a fly lead connecting any one or more of: the RF signal generator and the input node; the comparator output and the microprocessor input; the microprocessor's control output and the reference circuit; the RF signal generator and an antenna; and an antenna and the processor, each fly lead comprising a detachable connector.

8. The apparatus of claim 7, further comprising a calibration apparatus in which the antenna is connected to a connector having a connector input connectable, in use, to a corresponding connector of the fly lead and the calibration apparatus comprising:

switch means, being a solid-state switch, which is a single pole-four throw switch having four output terminals, interposed between an output of the connector and the antenna, the switch means having:

an input connected to the output of the connector;
a first output connected to the antenna;
a second output connected to an open circuit;
a third output connected to ground; and
a fourth output connected to a reference load, characterised in that:

the switch means is actuatable, in use, to selectively connect the connector to each of the four outputs individually such that, in use, the antenna can be calibrated relative to a signal transmission system connected to the input of the connector, and the reference load optionally comprising a substantially 50Ω load.

9. The apparatus of claim 8, wherein the switch means is adapted to cycle an input RF signal to each of its four outputs in sequence, such that measured responses for each switch position can be analysed and used in a calibration algorithm or matrix to calibrate the antenna and thereby factor-out variables associated with a connected signal transmission system.

10. The apparatus of claim 8, wherein the switch means further comprise a fifth output position, which connects the output of a first connector associated with a first antenna to an output of a second connector associated with a second antenna.

11. The apparatus of claim 1, wherein the RF signal generator comprises any one or more of the group consisting of:

a stable resonator circuit capable of outputting an RF signal having a substantially constant amplitude, frequency, and phase;

means for selectively adjusting any one or more of the amplitude, frequency, and phase of the RF signal at its output;

means for continuously adjusting any one or more of the frequency, amplitude, and phase of the RF signal at its output;

means for incrementally adjust any one or more of the frequency, amplitude, and phase of the RF signal at its output;

a plurality of resonators, each being configured to output a different frequency, amplitude and/or phase RF signal, and switch means for selectively connecting a selected one of the plurality of the resonators to the RF signal generator's output such that the RF signal generator can selectively output an RF signal having a selected frequency, amplitude and/or phase;

a plurality of frequency-matched antennas, each frequency-matched antenna being tuned to a particular bandwidth and wherein the RF signal generator is configured to output a corresponding plurality of narrow-bandwidth output signals to each of the frequency-matched antennas; and means for outputting a 1 to 10 ms burst signal, and wherein the processor is adapted to transpose the response signal from the time domain into the frequency domain to obtain a frequency spectrum from the burst signal, the processor being adapted to apply a Z-transform to derive from the response signal, a frequency spectrum.

12. The apparatus of claim 1, wherein the processor is adapted to verify the accuracy of the derived concentration of target substance by plotting the reflected response signal against the transmitted response signal, by checking that the data point for the derived target substance concentration falls within a statistically acceptable region of a calibrated target substance concentration scattergram.

13. The apparatus of claim 1, comprising a first antenna via which the output signal is sent, and a second antenna via which the transmitted and reflected response signals are received, the first and second antennas being placed side-by-side on one side of a target body part and wherein the first and second antennas are directional antennas such that, in use, the output signal is directed towards the second antenna, and such that the gain of the second antenna is biased towards the direction of the first antenna.

14. The apparatus of claim 1, wherein each antenna is a patch antenna disposed on the underside of a self-adhesive substrate, and wherein either:

a connector connected to the or each antenna is disposed on an upper surface of the self-adhesive substrate, and wherein the RF signal generator and processor are incorporated into the main body of a wrist-watch type device in which a complementary connector is provided on its underside for the or each connector, and wherein the wrist-watch type device further comprises a display for displaying the determined concentration of target substance in the patient's blood; or the patch antenna and is provided on an underside of a wrist-watch type device comprising the RF signal generator and processor and a display for displaying the determined concentration of target substance in the patient's blood, the patch antenna of the wrist-watch type device being held in contact with a patient's skin by a strap of the wrist-watch type device.

15. The apparatus of claim 1, comprising:

a main body comprising the at least one antenna operatively coupled, in use, to the skin of a patient; and a housing comprising at least one receiver antenna and/or reflector also operatively coupled, in use, to the skin of a patient, the housing being located, in use, on an opposite side of the patient's anatomy to the main body; and an adjustable strap connecting the main body to the housing, characterised in that:

the strap is formed as a pulley belt affixed at one end to the main body or housing, which is wound around respective rollers of the main body and the housing, and which has a free end, wherein the pulley belt and rollers are configured to centralise the housing relative to the main body such that pulling on the free end of the strap reduces the distance between the main body and the housing, whilst maintaining a substantially constant alignment between the main body and the housing, the rollers are rotatably affixed to the main body and housing, and wherein the strap is anchored at one end to the main body, and passes around a user's wrist or other body part to a first roller located to one side of the housing, wherein the strap folds back on itself and passes around the same side of the user's wrist or body part back towards the main body, wherein the strap extends around to the opposite side of the user's wrist or body part to a second roller located on an opposite side of the housing, such that an equal number of strap lengths are provided on either side of the user's wrist or body part, such that pulling on the free end of the strap causes movement of the housing relative to the main body whereby the strap lengths on either side of the user's wrist or body part are substantially equal, or equal.

16. The apparatus of claim 1, comprising:

a main body comprising the at least one antenna having a front surface operatively coupled, in use, to the skin of a patient; and an adjustable strap connected to the main body and extending, in use, around a part of the patient's body to retain the antenna adjacent the patient's skin, the non-invasive testing device further comprising:

an air bladder;

means for inflating the air bladder to cause the front surface of the antenna to press against the patient's skin with a predetermined force; and a pressure-relief valve interposed between the means for inflating and the air bladder.

17. The apparatus of claim 16, wherein the means for inflating the bladder comprises a manual pump, the manual pump comprising a compressible bladder with an outlet connected, via a one-way valve to an inlet of the air bladder.

18. The apparatus of claim 16, further comprising an air pressure sensor adapted, in use, to indicate when the air pressure within the air bladder is below an air pressure corresponding to the predetermined force.

19. The apparatus of claim 16, wherein the air bladder is interposed between the main body and a rear surface of the antenna.

20. The apparatus of claim 1, wherein the processor is either:

integrated into a main body portion of the non-invasive testing apparatus; or physically or logically separate from a main body of the non-invasive testing apparatus and comprising an I/O interface operatively connecting, in use, the driver and processor to a supplementary processing unit, the supplementary processing unit being located in any one or more of the group comprising:

a dedicated external processing unit;

a smartphone device;

a tablet computer device;

a personal computer; and on a cloud-based computer server.

* * * * *